United States Patent
Finison

(10) Patent No.: US 11,985,997 B2
(45) Date of Patent: May 21, 2024

(54) AUTOMATED SANITIZATION OF ROBOTIC FOOD EQUIPMENT USING ANTIMICROBIAL LIGHT

(71) Applicant: Ecolab USA Inc., St. Paul, MN (US)

(72) Inventor: Jeremy B. Finison, Rural Hall, NC (US)

(73) Assignee: Ecolab USA Inc., Saint Paul, MN (US)

( * ) Notice: Subject to any disclaimer, the term of this patent is extended or adjusted under 35 U.S.C. 154(b) by 389 days.

(21) Appl. No.: 17/101,449

(22) Filed: Nov. 23, 2020

(65) Prior Publication Data

US 2021/0153529 A1  May 27, 2021

Related U.S. Application Data

(60) Provisional application No. 62/940,543, filed on Nov. 26, 2019.

(51) Int. Cl.
*A23L 3/00* (2006.01)
*A23L 3/28* (2006.01)
(Continued)

(52) U.S. Cl.
CPC .................. *A23L 3/28* (2013.01); *A23L 3/001* (2013.01); *A23L 3/003* (2013.01); *A61L 2/084* (2013.01);
(Continued)

(58) Field of Classification Search
CPC .......... A23L 3/001; A23L 3/003; A23L 2/084; A61L 2/10; A61L 2/24
See application file for complete search history.

(56) References Cited

U.S. PATENT DOCUMENTS 6,524,529 B1  2/2003  Horton, III
6,573,663 B1  6/2003  MacGregor et al.
(Continued)

FOREIGN PATENT DOCUMENTS

CN  1653305 A  8/2005
CN  101452358 A  6/2009
(Continued)

OTHER PUBLICATIONS

International Preliminary Report on Patentability from International Application No. PCT/US2020/061760, dated Jun. 9, 2022, 9 pp.
(Continued)

*Primary Examiner* — Sean E Conley
(74) *Attorney, Agent, or Firm* — Fredrikson & Byron, P.A.

(57) ABSTRACT

An automated robotic food handling or preparation apparatus includes one or more food contact surfaces and an antimicrobial lighting fixture. The antimicrobial lighting fixture includes an enclosure forming a sanitization chamber and one or more antimicrobial lighting elements, wherein each element emits light at a wavelength, irradiance, and direction sufficient to inactivate one or more microorganisms on a target surface(s) within the sanitization chamber. The automated food handling apparatus subjects itself to an antimicrobial lighting treatment within the sanitization chamber upon detection of one or more conditions. The systems and/or methods of the present disclosure may sanitize food contact surfaces of automated robotic food equipment and help reduce the frequency at which such food contact surfaces need to be manually sanitized to keep microbial growth below acceptable levels.

23 Claims, 7 Drawing Sheets

(51) Int. Cl.
  *A61L 2/08* (2006.01)
  *A61L 2/10* (2006.01)
  *A61L 2/24* (2006.01)
(52) U.S. Cl.
  CPC .................. *A61L 2/10* (2013.01); *A61L 2/24* (2013.01); *A23V 2002/00* (2013.01); *A61L 2202/11* (2013.01); *A61L 2202/122* (2013.01); *A61L 2202/14* (2013.01)

(56) References Cited

U.S. PATENT DOCUMENTS

| | | | |
|---|---|---|---|
| 7,270,195 | B2 | 9/2007 | MacGregor et al. |
| 8,182,744 | B2 | 5/2012 | Mlodzinski et al. |
| 8,398,264 | B2 | 3/2013 | Anderson et al. |
| 8,581,882 | B2 | 11/2013 | Sohn et al. |
| 9,034,271 | B2 | 5/2015 | Shur et al. |
| 9,039,966 | B2 | 5/2015 | Anderson et al. |
| 9,700,641 | B2 | 7/2017 | Hawkins et al. |
| 9,839,706 | B2 | 12/2017 | Anderson et al. |
| 9,963,597 | B2 | 5/2018 | Aizenberg et al. |
| 10,232,066 | B2 | 3/2019 | Bailey |
| 10,773,690 | B2 | 9/2020 | Dellock et al. |
| 11,229,716 | B2 | 1/2022 | Vasilenko |
| 2002/0189270 | A1 | 12/2002 | Stensrud et al. |
| 2003/0127506 | A1* | 7/2003 | Braun, Jr. ............... A61L 2/202 232/31 |
| 2004/0175290 | A1 | 9/2004 | Scheir et al. |
| 2010/0303671 | A1 | 12/2010 | Bertrand |
| 2011/0216042 | A1 | 9/2011 | Wassvik et al. |
| 2012/0228645 | A1 | 9/2012 | Tu et al. |
| 2013/0224086 | A1 | 8/2013 | Stibich et al. |
| 2014/0060096 | A1 | 3/2014 | Shur et al. |
| 2014/0060104 | A1 | 3/2014 | Shur et al. |
| 2014/0264076 | A1 | 9/2014 | Bettles et al. |
| 2014/0300581 | A1 | 10/2014 | Aurongzeb et al. |
| 2015/0182647 | A1 | 7/2015 | Ranta et al. |
| 2016/0271803 | A1 | 9/2016 | Stewart |
| 2016/0375161 | A1 | 12/2016 | Hawkins et al. |
| 2017/0333582 | A1 | 11/2017 | Davis |
| 2017/0340761 | A1 | 11/2017 | Shur et al. |
| 2017/0368213 | A1 | 12/2017 | Mintie et al. |
| 2018/0046166 | A1 | 2/2018 | Kumar et al. |
| 2018/0113066 | A1 | 4/2018 | Freitag et al. |
| 2018/0117189 | A1 | 5/2018 | Yadav et al. |
| 2018/0117190 | A1 | 5/2018 | Bailey |
| 2018/0117193 | A1 | 5/2018 | Yadav et al. |
| 2018/0124883 | A1 | 5/2018 | Bailey |
| 2018/0126021 | A1 | 5/2018 | Valentine et al. |
| 2018/0154027 | A1 | 6/2018 | Anderson et al. |
| 2018/0243452 | A1 | 8/2018 | Hawkins et al. |
| 2018/0243453 | A1 | 8/2018 | Hawkins et al. |
| 2018/0345485 | A1 | 12/2018 | Sinnet et al. |
| 2018/0360077 | A1 | 12/2018 | Krebs et al. |
| 2019/0001930 | A1 | 1/2019 | Dellock et al. |
| 2019/0176338 | A1 | 6/2019 | Zito et al. |
| 2019/0298871 | A1 | 10/2019 | Dobrinsky |
| 2020/0205926 | A1 | 7/2020 | Keibel |
| 2020/0289683 | A1 | 9/2020 | Christian et al. |
| 2021/0000991 | A1 | 1/2021 | Kraus et al. |

FOREIGN PATENT DOCUMENTS

| | | | |
|---|---|---|---|
| CN | 101622016 | A | 1/2010 |
| CN | 204121454 | U | 1/2015 |
| CN | 104704067 | A | 6/2015 |
| CN | 104736261 | A | 6/2015 |
| CN | 105142682 | B | 12/2015 |
| CN | 105163605 | B | 12/2015 |
| CN | 204864170 | U | 12/2015 |
| CN | 105856259 | A | 8/2016 |
| CN | 105879148 | A | 8/2016 |
| CN | 105963730 | A | 9/2016 |
| CN | 205747250 | U | 11/2016 |
| CN | 106272467 | A | 1/2017 |
| CN | 206085069 | U | 4/2017 |
| CN | 206795846 | U | 12/2017 |
| CN | 108025182 | A | 5/2018 |
| CN | 108068125 | A | 5/2018 |
| CN | 207710799 | U | 8/2018 |
| CN | 108601376 | A | 9/2018 |
| CN | 108606754 | A | 10/2018 |
| CN | 108714884 | A | 10/2018 |
| CN | 208145201 | U * | 11/2018 |
| CN | 109065186 | A | 12/2018 |
| CN | 106444564 | B | 1/2019 |
| CN | 109131234 | A | 1/2019 |
| CN | 109202939 | A | 1/2019 |
| CN | 109276728 | A | 1/2019 |
| CN | 109316612 | A | 2/2019 |
| CN | 109431810 | A | 3/2019 |
| CN | 109481707 | A | 3/2019 |
| CN | 109481708 | A | 3/2019 |
| DE | 102017209966 | A1 | 12/2018 |
| EP | 3355940 | A2 | 8/2018 |
| JP | 2013104872 | A | 5/2013 |
| JP | 2015167470 | A | 9/2015 |
| JP | 2018117586 | A | 8/2018 |
| KR | 1499359 | B1 | 3/2015 |
| KR | 101616723 | B1 * | 4/2016 |
| KR | 1724447 | B1 | 4/2017 |
| WO | 2003096387 | A2 | 11/2003 |
| WO | 2006124211 | A1 | 11/2006 |
| WO | 2014036080 | A1 | 3/2014 |
| WO | 2015051024 | A1 | 4/2015 |
| WO | 2014036080 | A9 | 5/2015 |
| WO | 2017062260 | A2 | 4/2017 |
| WO | 2018087171 | A1 | 5/2018 |
| WO | 2018122009 | A1 | 7/2018 |

OTHER PUBLICATIONS

Office Action from U.S. Appl. No. 16/818,138, dated May 24, 2022, 13 pp.
Response to Office Action dated Aug. 22, 2022 from U.S. Appl. No. 16/918,644, filed Nov. 22, 2022, 12 pp.
International Search Report and Written Opinion of International Application No. PCT/US2020/061760, dated Mar. 18, 2021, 14 pp.
Advisory Action from U.S. Appl. No. 16/918,644, dated Apr. 17, 2023, 2 pp.
Response to Final Office Action dated Feb. 6, 2023 from U.S. Appl. No. 16/918,644, filed Apr. 4, 2023, 12 pp.
Office Action from U.S. Appl. No. 16/918,644 dated Aug. 22, 2022, 14 pp.
Response to Office Action dated May 24, 2022 from U.S. Appl. No. 16/818,138, filed Aug. 24, 2022, 14 pp.
Response to Communication Pursuant to Rules 161(1) and 162 EPC dated Jan. 12, 2023, from counterpart European Application No. 20828601.3, filed Jul. 5, 2022, 15 pp.
First Office Action and Search Report, and translation thereof, from counterpart Chinese Application No. 202080077669.4 dated Jun. 6, 2023, 25 pp.
"Hubbell Lighting Secures Licensing Agreement with the University of Strathclyde High Intensity Narrow Spectrum Technology," Hubbell Lighting, May 4, 2018, 3 pp.
"Hubbell Lighting to Integrate Bacteria Suppressing Technology into Smart Luminaires," http://www.lightingdesignandspecification.ca/changing-scene/2322-hubbe, Jun. 1, 2018, 1 pp.
"Ice UV," retrieved from https://www.freshaireuv.com/ice-machines/ on Feb. 22, 2019, 5 pp.
"LG Electronics LP153HD3B Installation Guide," retrieved from manualzz.com/doc/4030343/lg-electronics-lp153hd3b-installation-guide on May 11, 2020, 2 pp.
"Light Fixture Kills Bacteria Safely, Continuously," Science Daily, Jun. 26, 2015, 2 pp.
"Single Color Outdoor Weatherproof LED Flexible Lightstrip Part Number WFLS-x," https://d114hh0cykhyb0.cloudfront.net/pdfs/WFLS-x.pdf, Apr. 21, 2014, 2 pp.
"Wireless LED 4 Channel EZ Dimmer Controller with Channel Pairing," https://www.superbrightleds.comjmoreinfojrgb-led-controllers/wireless-4-channelrgb-led-dimmer-receiver/3372/7141/#tab/Reviews, Jul. 17, 2018, 7 pp.

(56) References Cited

OTHER PUBLICATIONS

Endarko et al., "High-Intensity 405 nm Light Inactivation of Listeria Monocytogenes," Photochemistry and Photobiology, vol. 88, No. 5, Sep.-Oct. 2012, pp. 1280-1286.
Gunther et al., "The Effects of 405-nm Visible Light on the Survival of Campylobacter on Chicken Skin and Stainless Steel," Foodborne Pathogens and Disease, vol. 13, No. 5, May 2016, 6 pp.
Kim et al., "Antibacterial Effect and Mechanism of High-Intensity 405 ± 5 nm Light Emitting Diode on Bacillus Cereus, Listeria Monocytogenes, and *Staphylococcus aureus* Under Refrigerated Condition," Journal of Photochemistry and Photobiology B: Biology, vol. 153, Dec. 2015, pp. 33-39.
Kingsley et al., "Evaluation of 405-nm Monochromatic Light for Inactivation of Tulane Virus on Blueberry Surfaces," Journal of Applied Microbiology, vol. 124, No. 4, Apr. 2018, pp. 1017-1022.
Lacombe et al., "Reduction of Bacterial Pathogens and Potential Surrogates on the Surface of Almonds Using High-Intensity 405-nanometer light," Journal of Food Protection, vol. 79, No. 11, Nov. 2016, pp. 1840-1845.
Liang et al., "Blue Light Induced Free Radicals from Riboflavin on *E. coli* DNA Damage," Journal of Photochemistry and Photobiology B: Biology, vol. 119, Dec. 29, 2012, pp. 60-64.
Maclean et al., "High-Intensity Narrow-Spectrum Light Inactivation and Wavelength Sensitivity of *Staphylococcus aureus*," Federation of European Microbiological Societies, Jun. 16, 2008, pp. 227-232.
Maclean et al., "Sporicidal Effects of High-Intensity 405 nm Visible Light on Endospore-Forming Bacteria," Photochemistry and Photobiology, vol. 89, No. 1, Jan./Feb. 2013, pp. 120-126.
Mcdonald et al., "405 nm Light Exposure of Osteoblasts and Inactivation of Bacterial Isolates from Arthroplasty Patients: Potential for New Disinfection Applications?", European Cells and Materials, vol. 25, Mar. 7, 2013, pp. 204-214.
Murdoch et al., "Bactericidal Effects of 405nm Light Exposure Demonstrated by Inactivation of *Escherichia, Salmonella, Shigella, Listeria,* and*Mycobacterium* Species in Liquid Suspensions and on Exposed Surfaces," The Scientific World Journal, vol. 2012, Apr. 1, 2012, 8 pp.
Murdoch et al., "Inactivation of Campylobacter Jejuni by Exposure to High-Intensity 405-nm Visible Light," Foodborne Pathogens and Disease, vol. 7, No. 10, Oct. 2010, pp. 1211-1216.
Ramakrishnan et al., "Differential Sensitivity of Osteoblasts and Bacterial Pathogens to 405-nm Light Highlighting Potential for Decontamination Applications in Orthopedic Surgery," Journal of Biomedical Optics, vol. 9, No. 10, Oct. 2014, 8 pp.
Roh et al., "Blue Light-Emitting Diode Photoinactivation Inhibits Edwardsiellosis in Fancy Carp (*Cyprinus carpio*)," Aquaculture, vol. 483, Jan. 20, 2018, pp. 1-7.
Notice of Allowance from U.S. Appl. No. 16/818,138 dated Oct. 20, 2022, 10 pp.
Final Office Action from U.S. Appl. No. 16/918,644 dated Feb. 6, 2023, 18 pp.

\* cited by examiner

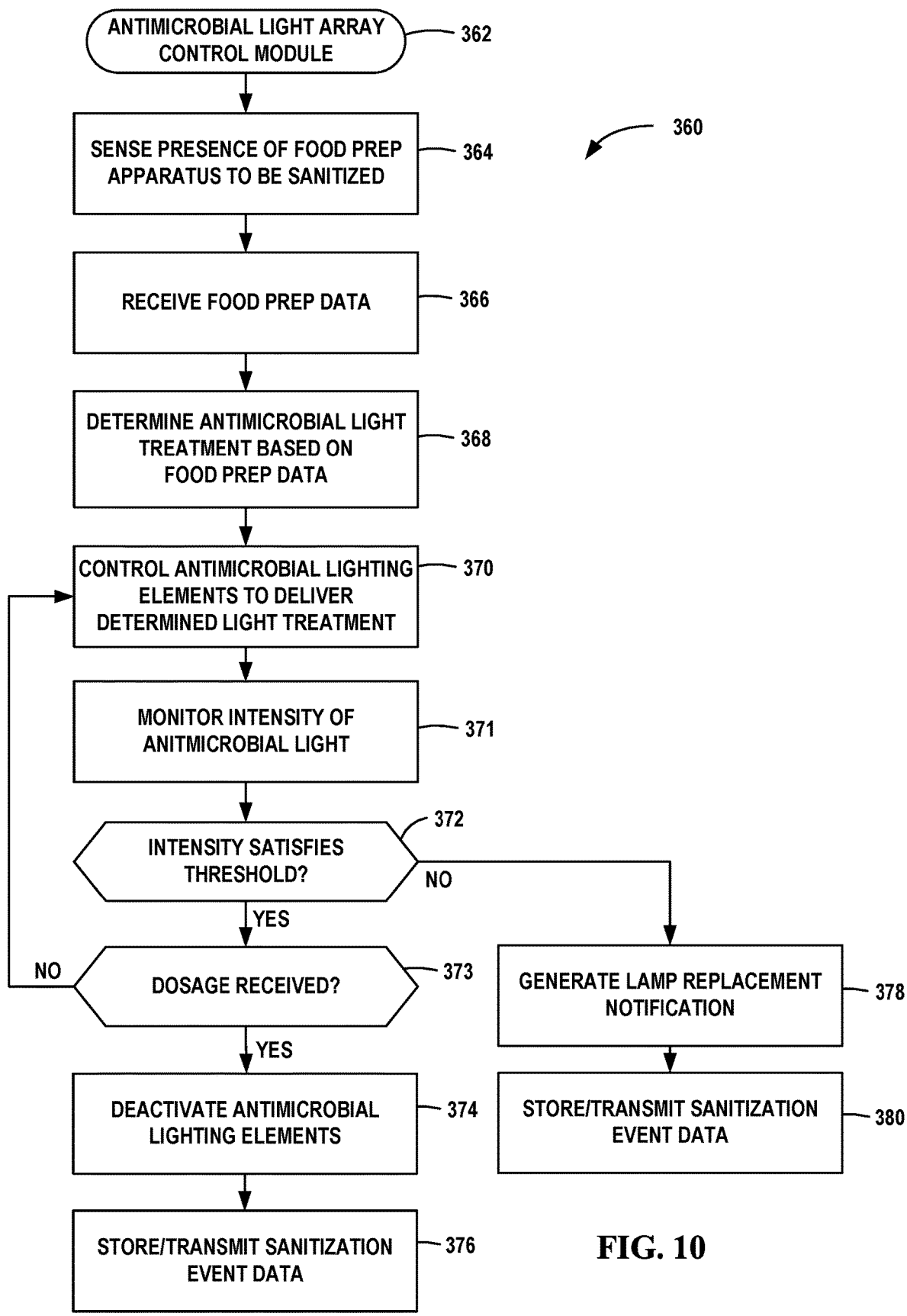

ated food preparation apparatus. Each of the one or more
AUTOMATED SANITIZATION OF ROBOTIC FOOD EQUIPMENT USING ANTIMICROBIAL LIGHT This application claims the benefit of U.S. Provisional Application No. 62/940,543, titled, "AUTOMATED SANITIZATION OF ROBOTIC FOOD EQUIPMENT USING ANTIMICROBIAL LIGHT", filed Nov. 26, 2019, the entire content of which is incorporated herein by reference.

TECHNICAL FIELD

The disclosure relates to systems and methods of reducing microbial growth on environmental surfaces.

BACKGROUND

Contamination of environmental surfaces poses a risk for transmission of pathogens and other microorganisms. Bacteria and other harmful microorganisms can survive for extended periods of time on environmental surfaces. The microorganism can include pathogenic microorganisms, such as gram-positive and gram-negative bacteria, yeasts, fungi, viruses, mold, and parasites. Various illness-causing pathogens, such as *Bacillus* spp., *Pseudomonas* spp., *Listeria monocytogenes, Staphylococcus aureus, Salmonella* spp., *E. coli*, coliforms, *Legionella* spp., *Acinetobacter* species, *Candida* spp., *Saccharomyces* spp., *Aspergillus* spp., *Alcaligenes, Flavobacterium, Campylobacter* spp., *Clostridium perfringens, Clostridium botulinum, Shigella* spp., *Vibrio* spp., noroviruses, hepatitis A and the like, may be transmitted to food from contaminated environmental surfaces such as food contact surfaces of equipment or utensils. At certain levels, the presence of microorganisms on food contact surfaces of equipment or utensils may result in consumer perception of a lower quality product, regulatory investigations and sanctions, individual cases of pathogen-based illness, and foodborne illness outbreaks.

SUMMARY

In general, the disclosure is directed to systems and/or methods of reducing microbial growth on food contact surfaces of equipment or utensils. The system may include an automated robotic food handling or processing apparatus including one or more food contact surfaces and an antimicrobial lighting fixture including an enclosure forming a sanitization chamber. The antimicrobial lighting fixture includes one or more antimicrobial lighting elements, wherein each element emits light at a wavelength, irradiance, and direction sufficient to inactivate one or more microorganisms on a target surface(s). The systems and/or methods of the present disclosure may sanitize food contact surfaces of automated robotic food equipment and help reduce the frequency at which such food contact surfaces need to be manually sanitized to keep microbial growth below acceptable levels.

In one example, the disclosure is directed to a system comprising: an antimicrobial lighting fixture including: an enclosure forming a sanitization chamber; and one or more antimicrobial lighting segments, each antimicrobial lighting segment including one or more elements, wherein each element emits light within the sanitization chamber at a wavelength, irradiance, and direction sufficient to inactivate one or more microorganisms on a target surface within the sanitization chamber; and an automated food preparation apparatus including: at least one mechanical component controllable to prepare at least one food item and comprising at least one food contact surface; and a controller comprising computer readable instructions configured to be executed on one or more processors to control at least one mechanical component to move at least one food contact surface from a food preparation position to a sanitization position within the sanitization chamber.

Each antimicrobial light segment may be controlled based on food preparation information received from the automated food preparation apparatus. Each of the one or more antimicrobial lighting segments may be individually controllable by the antimicrobial lighting fixture. The antimicrobial lighting fixture may further include a presence sensor that detects presence of at least a portion of the automated food preparation apparatus within the sanitization chamber. The antimicrobial lighting fixture may further include one or more sensors that detect an intensity of antimicrobial light emitted within the sanitization chamber.

The antimicrobial lighting fixture may further include a controller connected to receive the detected intensity of the antimicrobial light emitted within the sanitization chamber and that generates a lamp replacement notification when the detected intensity is below a threshold. The antimicrobial lighting fixture may further include a controller connected to receive the detected intensity of the antimicrobial light emitted within the sanitization chamber and that controls a duration of an antimicrobial light treatment received within the sanitization chamber by the at least one food contact surface of the automated food preparation apparatus based on the detected intensity.

The automated food preparation apparatus may include a plurality of food contact surfaces, and wherein the one or more antimicrobial lighting segments are controllable to direct light at a wavelength and irradiance sufficient to inactivate one or more microorganisms on one or more of the plurality of food contact surfaces when the one or more food contact surfaces are present within the sanitization chamber.

At least one of the antimicrobial lighting segments may include a plurality of light-emitting diode (LED) elements, and wherein each LED element emits light including wavelengths in a range of about 405±15 nanometers. At least one of the antimicrobial lighting segments may include one or more lighting elements that emit light in a short-wavelength ultraviolet (UV-C) wavelength range of 200-300 nm. At least one of the antimicrobial lighting segments may include one or more elements that emits light including one or more wavelengths in a first wavelength range and at least one other of the antimicrobial lighting segments includes one or more elements that emit light including one or more wavelengths in a second wavelength range.

The one or more microorganisms may include at least one of *Bacillus* spp., *Pseudomonas* spp., *Listeria, Staphylococcus aureus, Salmonella* spp., *E. coli*, coliforms, *Legionella* spp., *Acinetobacter* species, *Candida* spp., *Saccharomyces* spp., *Aspergillus* spp., *Alcaligenes, Flavobacterium, Campylobacter* spp., *Clostridium perfringens, Clostridium botulinum, Shigella* spp., *Vibrio* spp., noroviruses, or hepatitis A.

In another example, the disclosure is directed to a method comprising: controlling at least one mechanical component of a food preparation apparatus having at least one food contact surface to prepare at least one food item at a food preparation area during a food preparation process; determining at least one food preparation timer based on one or more parameters of the food preparation process; monitoring a duration of the food preparation process; comparing the duration of the food preparation process to the food preparation timer; and initiating a sanitization event when the duration of the food preparation process satisfies the food preparation timer, wherein initiating the sanitization event includes: controlling the at least one mechanical component of the food preparation apparatus to move the at least one food contact surface from one of a plurality of food preparation positions with respect to the food preparation area to a sanitization position within a sanitization chamber of an antimicrobial lighting fixture.

The method may further include monitoring a duration of an antimicrobial light treatment received within the sanitization chamber. The method may further include monitoring an intensity of an antimicrobial light treatment received within the sanitization chamber. The method may further include controlling the at least one mechanical component of the food preparation apparatus to move the at least one food contact surface from the sanitization position within the sanitization chamber of the antimicrobial lighting fixture to one of the plurality of food preparation positions with respect to the food preparation area based on the monitored intensity of the antimicrobial light treatment. The method may further include determining a dosage of antimicrobial light received based on the monitored intensity of the antimicrobial light treatment. The one or more parameters of the food preparation process may include a type of the at least one food item.

In another example, the disclosure is directed to a nonvolatile computer-readable storage medium storing instructions that, when executed, cause one or more processors to: control at least one mechanical component of a food preparation apparatus having at least one food contact surface to prepare at least one food item at a food preparation area during a food preparation process; determine at least one food preparation timer based on one or more parameters of the food preparation process; monitor a duration of the food preparation process; compare the duration of the food preparation process to the food preparation timer; and initiate a sanitization event when the duration of the food preparation process satisfies the food preparation timer, wherein initiating the sanitization event includes: controlling the at least one mechanical component of the food preparation apparatus to move the at least one food contact surface from one of a plurality of food preparation positions with respect to the food preparation area to a sanitization position within a sanitization chamber of an antimicrobial lighting fixture.

The nonvolatile computer-readable storage medium may further store instructions that, when executed, cause the one or more processors to: control the at least one mechanical component of the food preparation apparatus to move the at least one food contact surface from the sanitization position within the sanitization chamber of the antimicrobial lighting fixture to one of the plurality of food preparation positions with respect to the food preparation area based on the monitored intensity of the antimicrobial light treatment.

The details of one or more examples are set forth in the accompanying drawings and the description below. Other features and advantages will be apparent from the description and drawings, and from the claims.

BRIEF DESCRIPTION OF DRAWINGS

FIG. 10 is a flow chart showing an example process by which an antimicrobial lighting fixture may execute a sanitization event in accordance with the present disclosure.

DETAILED DESCRIPTION

Figure 1:
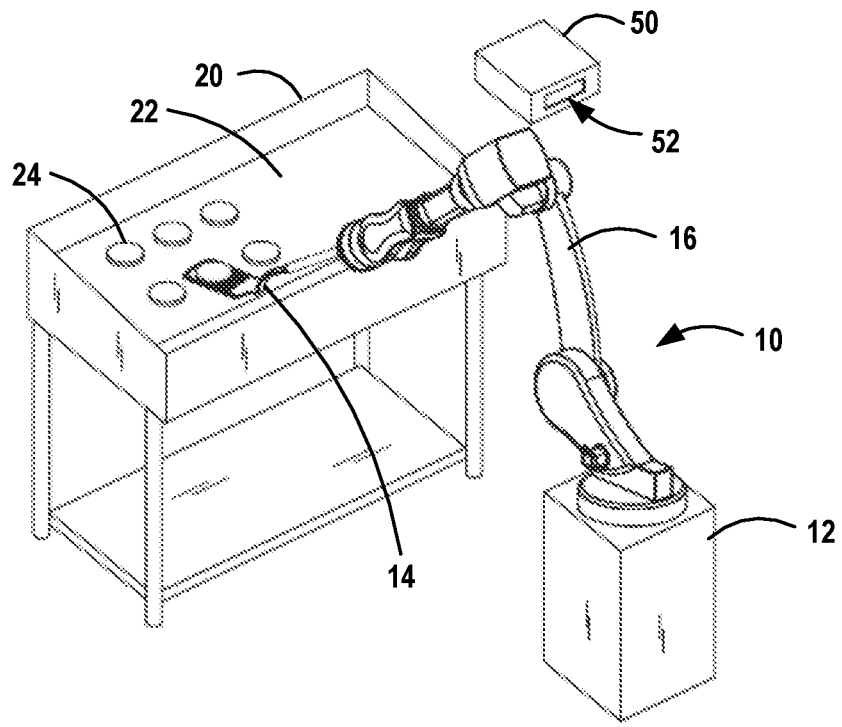
FIG. 1 is a diagram illustrating an example automated food service robot working in an example food handling and/or preparation environment and an example antimicrobial lighting fixture in accordance with the present disclosure.

The Centers for Disease Control and Prevention (CDC) has identified contaminated equipment as one of five broad categories of contributing factors that directly relate to food safety concerns within retail and food service establishments. Federal, state and local guidelines set forth procedures for the cleaning and sanitizing of food contact surfaces of equipment and utensils in a manner to prevent transmission of foodborne pathogens or contamination.

The food service industry is moving toward utilization of automated robotic equipment in food handling, preparation and processing operations. The same safety measures designed for food contact surfaces of equipment or utensils may also apply to food contact surfaces of such automated robotic food equipment. However, the complex designs and often stationary nature of such automated robotic food equipment may present obstacles to effective cleaning and/or sanitization.

In general, the disclosure is directed to systems and/or methods of reducing microbial growth on surfaces, such as food contact and/or other surfaces, of automated robotic food equipment. The systems and/or methods of the present disclosure may help to reduce or control microbial growth on the food contact surfaces of the automated robotic food equipment, supplement manual cleaning and/or sanitization of food contact surfaces of automated robotic food equipment, and/or help reduce the frequency at which such food contact surfaces need to be manually sanitized to keep microbial growth below acceptable levels.

The systems/methods of the present disclosure may include an automated food handling or preparation apparatus (also referred to herein as automated food equipment, an automated food service robot or a food service robot) including one or more food contact surfaces and an antimicrobial lighting fixture. The antimicrobial lighting fixture includes one or more antimicrobial lighting elements, wherein each element emits light at a wavelength, irradiance, and direction sufficient to inactivate one or more microorganisms on a target surface(s). The automated food service robot and/or the antimicrobial lighting fixture are configured to automatically expose one or more food contact surfaces of the automated food equipment upon detection of one or more conditions. The systems and/or methods of the present disclosure may sanitize one or more food contact surfaces on automated food equipment and help reduce the frequency at which such food contact surfaces need to be manually sanitized to keep microbial growth below acceptable levels.

Ultraviolet (UV) light, including germicidal ultraviolet light having wavelengths in a range of about 200-300 nanometers (nm) (also known as short-wavelength ultraviolet or UV-C), and light having wavelengths in a range of about 405±10 nm, have been demonstrated to decontaminate the air and exposed surfaces by inactivating microorganisms. The systems and methods in accordance with the present disclosure concern the strategic application and control of an antimicrobial lighting system to food contact surfaces of an automated food handling or preparation apparatus, such as an automated food service robot.

For purposes of the present disclosure, the term "antimicrobial light" will be used generally to refer to light including UV light having wavelengths anywhere in a first wavelength range of 200-300 nm and/or light having wavelengths anywhere in a second wavelength range of 405±15 nm (i.e., between about 390-420 nm) and having a peak wavelength of about 405 nm, and having sufficient irradiance (power received by a surface per unit area) of these wavelengths as measured at a target surface to result in inactivation of one or more microorganisms at the target surface within a desired period of time. In some examples, the first wavelength range may include wavelengths anywhere in a range of about 254±5 nm (i.e., between about 249-259 nm).

In some examples, an antimicrobial light fixture may include one or more light source elements, such as mercury-based lamps, LEDs or other light source elements, that emit UV light at wavelengths anywhere between about 254±5 nm and/or may include one or more light source elements, such as light-emitting diodes (LEDs) or other light source elements, that emit light at wavelengths anywhere between about 405±15 nm. It shall be understood that the particular peak wavelength or range of wavelengths emitted by the element(s) of each antimicrobial lighting source may vary somewhat from these stated ranges, depending, for example, on the response curve for each particular lighting element, and the disclosure is not limited in this respect. Also, each element does not necessarily emit light across the entire wavelength range. In general, the antimicrobial light emitted contains at least some of these wavelengths at a sufficient intensity to effect inactivation of one or more microorganisms on a target surface within a desired period of time.

In some examples, the antimicrobial light may also include light of other wavelengths, such as visible light including wavelengths anywhere between about 380 to 740 nm. The intensity of the visible light may be sufficient for illumination when viewed by the human eye. The visible light and the antimicrobial light may be emitted from the same light source elements or from different light source elements.

An antimicrobial lighting fixture may include a housing or enclosure and an array of one or more individually controllable antimicrobial light segments. The enclosure forms a sanitization chamber sized to receive at least the food contact surfaces of an automated food service robot. Each antimicrobial light segment may include one or more light emitting elements, such an LED light strip, wherein each of the light emitting elements emits antimicrobial light at a wavelength and irradiance sufficient to inactivate one or more microorganisms on a target surface within the antimicrobial chamber within a defined period of time. Other examples may include LED tube lights, light bars, rope lights, lamps, bulbs, individual light emitting elements, and any other flexible or inflexible light element configuration or shape. Each individual light element may be directional or omnidirectional. The light segments may be customized in size and shape to both fit within an enclosure of the antimicrobial lighting fixture and to provide sufficient irradiance at one or more target surfaces of an automated food service robot positioned within the enclosure to achieve a desired level of microbial inactivation at those surfaces, or to prevent microbial growth at those surfaces, within a defined period of time.

In some examples, some of the individually controllable antimicrobial light segments emit light at wavelengths anywhere in a first wavelength range of 254±5 nm and other of the individually controllable antimicrobial light segments emit ultraviolet light having wavelengths anywhere in a second wavelength range of 405±15 nm. In this way, antimicrobial light in the first wavelength range may be used for more rapid kill (minutes or seconds) and antimicrobial light in the second wavelength range may be used for safer but longer dwell times (hours). The wavelength(s) of the antimicrobial light emitted by the antimicrobial lighting fixture may depend in part on the type of microorganism(s) to be targeted, and this may depend in part on the type(s) of food prepared by the food service robot, and on other factors. In some examples, the wavelength(s) of the antimicrobial light may also be controlled in order to limit human exposure to ultraviolet wavelengths.

In some examples, the enclosure of the antimicrobial lighting fixture forms a sanitization chamber and includes an entrance opening or slot through which one or more food contact surfaces of an automated food service robot may be received into the sanitization chamber. The enclosure may further include any one or more of drapes, barriers, shields or other means of reducing the risk of possible human exposure to the antimicrobial light emitted within the sanitization chamber.

A motion sensor associated with the antimicrobial lighting fixture may detect presence of an automated food service robot at or near the entrance to the enclosure, or within the sanitization chamber, and the antimicrobial lighting fixture may enable one or more of antimicrobial light segments to irradiate the portions of the food service robot within the chamber based on the detected presence information.

The frequency at which the automated food service robot should execute a sanitization procedure may be based on food preparation information received with respect to the associated automated food service robot. The food preparation information may include, for example, time of day, the type of food being prepared, the amount of time a food service robot has been preparing food, the amount of time since the last sanitization procedure was performed, and other factors. The antimicrobial light fixture may receive usage data regarding the automated food service robot, and may be controlled based on the received usage data. For example, the light array may control the length of the sanitization procedure or the intensity of the emitted light based on time of day information, food type information, time of use information, or other information related to usage of the automated food service robot.

The automated food service robot may include at least one food contact surface, and may include multiple food contact surfaces. According to the 2017 United States FDA Food Code, the term "food-contact surface" means: (1) a surface of equipment or a utensil with which food normally comes into contact; or, (2) a surface of equipment or a utensil from which food may drain, drip, or splash: (a) into a food; or (b) onto a surface normally in contact with food.

Within the sanitization chamber of the antimicrobial lighting fixture, one or more target food contact surface(s) on the automated food service robot are irradiated with light of an antimicrobial wavelength at a sufficient dosage to effect microbial inactivation on the identified target surfaces. Other surfaces present within the sanitization chamber may also be irradiated with antimicrobial light. The dosage may be defined as the irradiance, or the power received by a surface per unit area (e.g., as measured in watts per square centimeter, $W/cm^2$) of the antimicrobial wavelength(s) measured at the target surface. The irradiance is dependent at least in part by the power applied to the light source(s), the distance from the light source to the surface, the total surface area illuminated, and the time of exposure.

In some examples, it is not necessary to continuously illuminate all food contact surfaces on the automated food service robot, nor is it necessary to illuminate all food contact surfaces at the same time or at the same dose. For example, the antimicrobial light treatment protocol may include a high exposure setting (full power on or highest intensity and/or longer exposure time) antimicrobial cycle mode that occurs when usage of the food service robot is predicted to be in an unused state (at night, or during times at which a restaurant is closed, for example). The antimicrobial light treatment protocol may also include a reduced power mode or modified setting in which one or more of the antimicrobial light segments are selectively controlled to output at a reduced intensity, such as to reduce exposure risk when humans are likely to be present, but at a level that is sufficient to inactivate one or more microorganisms at the food contact surface(s) over a defined period of time.

In another example, when the automated food service robot is experiencing high frequency of use the antimicrobial lighting system may switch to a high power (high intensity or high sanitizing) mode. For example, in a self-service restaurant environment during high usage times, the antimicrobial lighting fixture may include a high intensity sanitizing mode. The high intensity sanitizing mode may increase the intensity and/or selectively apply one or more wavelengths of the antimicrobial light so as to accomplish faster sanitization of the target food contact surfaces during high usage times. The high intensity sanitizing mode may also increase the frequency at which the automated food service robot initiates and completes a sanitization procedure by subjecting the one or more food contact surfaces to the antimicrobial light within the sanitization chamber.

The antimicrobial lighting systems may include lighting segments and/or lighting elements that output light at antimicrobial wavelengths alone or in combination with light of other wavelengths (e.g., one or more wavelengths of ultraviolet light and/or one or more wavelengths of visible light). For example, some lighting segments or lighting elements may output antimicrobial light while other lighting segments or lighting elements output light within the visible spectrum.

An antimicrobial light array may be installed and configured with respect to the interior of the sanitization chamber such that there is overlapping illumination from each successive lighting element within the chamber. This area of illumination irradiates a surface area dependent upon the design and physical arrangement of the individual light elements in each lighting segment and the distance of the element(s) from the probable locations of the target surface(s) within the chamber. It shall be understood that the irradiance power at the surface being treated is dependent upon the distance between the emitter and the target surface. The design and installation of the light array within the chamber is such that the power of the antimicrobial light is controlled such that sufficient irradiance required for microbiological mitigation within the desired time period, at the probable locations of the target surfaces when placed within the chamber, is achieved. It shall further be understood that the time/irradiance/distance power relationship required for microbiological mitigation depends upon the target organism(s).

LED lifetime of the antimicrobial lighting elements can range from hundreds to in excess of 100,000 hours of operation. Furthermore, the emitted power of the lamp can be modulated using a Pulse-Width-Modulation (PWM) technique to achieve higher irradiant power without stressing the antimicrobial light to the extent that the light's lifetime is adversely affected when operated under constant power. The frequency and duty cycle applied to the antimicrobial light segments may be modulated to achieve the desired irradiance power at the target surface(s). PWM enables the color temperature (spectral distribution) of the LED lamp to be maintained while varying the observed lamp brightness.

In some examples, antimicrobial light segments may be fabricated from, for example, flexible LED light strips. In some examples, the antimicrobial light segments include at least some light elements that emit wavelengths in a first antimicrobial range of about 405±10 nm and/or include at least some light elements that emit wavelengths in a second antimicrobial range of about 254±5 nanometers. Such antimicrobial light segments may be configured and arranged within the sanitization chamber to treat one or more food contact surface(s) on portions of an automated food service robot received within the sanitization chamber. As mentioned above, food contact surfaces may include (1) a surface of an automated food service robot with which food normally comes into contact; or, (2) a surface of an automated food service robot from which food may drain, drip, or splash: (a) into a food; or (b) onto a surface normally in contact with food. Other non-food contact surfaces in addition to food contact surfaces may also be irradiated by the antimicrobial light segments when present within the sanitization chamber.

Organisms that may be present on food contact and/or non-food contact surfaces of an automated food service robot, and that may be inactivated using the antimicrobial lighting systems and methods of the present disclosure include, but are not limited to, bacteria, viruses, yeasts, and molds, such as *Bacillus* spp., *Pseudomonas* spp., *Listeria monocytogenes, Staphylococcus aureus, Salmonella* spp., *E. coli*, coliforms, *Legionella* spp., *Acinetobacter* species, *Candida* spp., *Saccharomyces* spp., *Aspergillus* spp., *Alcaligenes, Flavobacterium, Campylobacter* spp., *Clostridium perfringens, Clostridium botulinum, Shigella* spp., *Vibrio* spp., noroviruses, hepatitis A and any other pathogen or microorganism that may be encountered in such environments.

FIG. 1 is a diagram illustrating an example automated food service robot 10 at work within a food service environment and an example antimicrobial lighting fixture 50 in accordance with the present disclosure. In this example, antimicrobial lighting fixture 50 including a housing forming a cavity and including one or more antimicrobial lighting elements and/or antimicrobial light segments (not shown in FIG. 1). Food service robot may be stationary or moveable, either manually or automatically, as discussed herein below. Antimicrobial lighting fixture may also be stationary or moveable, either manually or automatically. One or both of food service robot and/or antimicrobial lighting fixture may be moveable (either manually or automatically) to irradiate at least the food contact surfaces of food service robot with antimicrobial light.

In the example of FIG. 1, food service robot 10 includes a stationary base 12, an articulated robotic arm 16 and a utensil attachment 14. In other examples, base 12 may be mobile and include wheels or tracks such that food service robot 10 may be mobile (either manually or automatically) and may move between multiple locations within a food service environment and/or with respect to antimicrobial lighting fixture 50. Similarly, antimicrobial lighting fixture may also be stationary or mobile, either manually or automatically. Thus, although FIG. 1 will be described with respect to a stationary food service robot, it shall be understood that the disclosure is not limited in this respect.

Although a stationary antimicrobial fixture 50 is shown in FIG. 1, it shall be understood that the antimicrobial lighting fixture 40 could be mobile and be positioned, either by human interaction or self-controlled, to irradiate at least the food contact surfaces of food service robot with antimicrobial light.

In the example of FIG. 1, automated food service robot 10 is in a food prep mode that includes working at a food appliance 20 (a grill in this example) having a food preparation area or surface 22 at which one or more articles of food 24 are being prepared. Food preparation area 22 may include any area, appliance or machine at which food may be prepared, including cutting boards, counter tops, grills, fryers, stoves, ovens, etc. Food service robot 10 includes a removable utensil attachment 14 (in this example, a turner or spatula) that is used during the food handling/preparation process. Utensil attachment 14 may include any number of food handling or preparation tools, including but not limited to spatulas, turners, forks, tongs, knives, cutters, scrapers, sifters, ladles, measuring cups or spoons, scoops, whisks, blenders, and the like.

Figure 2:
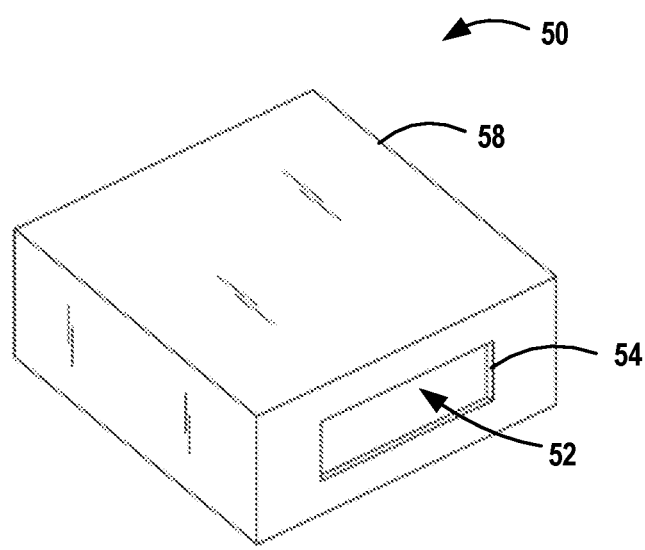
FIG. 2 is a diagram illustrating the example antimicrobial lighting fixture of FIG. 1 in accordance with the present disclosure.

FIG. 2 is a diagram illustrating the example antimicrobial lighting fixture 50 of FIG. 1. Enclosure 58 includes an opening or slot 54 that forms an entrance into sanitization chamber 52. Slot 54 is sized such that one or more food contact surfaces to be sanitized, such as at least a portion of utensil attachment 14 and/or other portion of food service robot, may be received into the sanitization chamber 52. Enclosure 58 forms sanitization chamber 52. Antimicrobial lighting fixture includes one or more antimicrobial light elements and/or antimicrobial lighting segments positioned within the enclosure 58 so as to irradiate one or more food contact surfaces within the chamber with antimicrobial light.

Within the example food preparation environment shown in FIG. 1, antimicrobial lighting fixture 50 is positioned with respect to food service robot 10 such that food service robot 10 may insert, for example, at least a portion of utensil attachment 14 into sanitization chamber 52 such that one or more food contact surfaces (and/or any non-food contact surfaces present within the chamber) may be irradiated with antimicrobial light within sanitization chamber 52.

In some examples, it may be desirable to arrange the one or more antimicrobial lighting elements and/or lighting arrays to provide substantially evenly distributed antimicrobial irradiation within antimicrobial lighting chamber 52. In other examples, it may be desirable to provide relatively higher intensity antimicrobial irradiation at certain areas or zones within the chamber 52, such as those areas or zones including the probable locations of the food contact surfaces to be sanitized. In other examples, it may be desirable to provide irradiation in a first antimicrobial wavelength range based on a first set of predetermined conditions, and to provide irradiation in a second antimicrobial wavelength range based on a second set of predetermined conditions. It shall be understood, therefore, that the antimicrobial irradiation within antimicrobial lighting chamber 52 may be varied depending upon several factors, such as the application and/or the environment in which antimicrobial lighting fixture is to be used, the type of food service robot and/or food contact surfaces to be sanitized, the type of food to be handled and/or prepared, the usage patterns for the food service robot, the time of day, manual cleaning and sanitization protocols, and other factors, and that the disclosure is not limited in this respect.

In some examples, the antimicrobial lighting elements may be arranged within the antimicrobial lighting chamber to provide simultaneous antimicrobial illumination of target surfaces of the food service robot from multiple directions. For example, for a box-shaped chamber, one or more antimicrobial lighting elements, arranged individually, in segments or in a grid, may be provided on one or more interior surfaces of the housing. As another example, one or more antimicrobial lighting elements may be provided in a ring or donut shape to irradiate target surfaces of a food service robot from multiple directions. In other examples, the food service robot itself may rotate or move within the sanitization chamber to expose target surfaces to antimicrobial light within the chamber. Although a closed sanitization chamber 50 is shown and described herein for example purposes, it shall be understood that sanitization chamber may take any desired shape, and that sanitization chamber need not be entirely closed or provide antimicrobial illumination of a target object from multiple directions, and that the disclosure is not limited in this respect. As another example, antimicrobial lighting fixture 50 may include one or more antimicrobial lighting elements that direct antimicrobial light toward a 2-dimensional target area (rather than within an enclosed chamber) from one side or direction, or from two or more sides or directions, rather than from multiple directions within an enclosed chamber. It shall be understood, therefore, that many alternative examples and configurations may be used for the antimicrobial lighting fixture in terms of the enclosure or target surface area and also in terms of the arrangement of the antimicrobial lighting elements and/or lighting segments.

Figure 3:
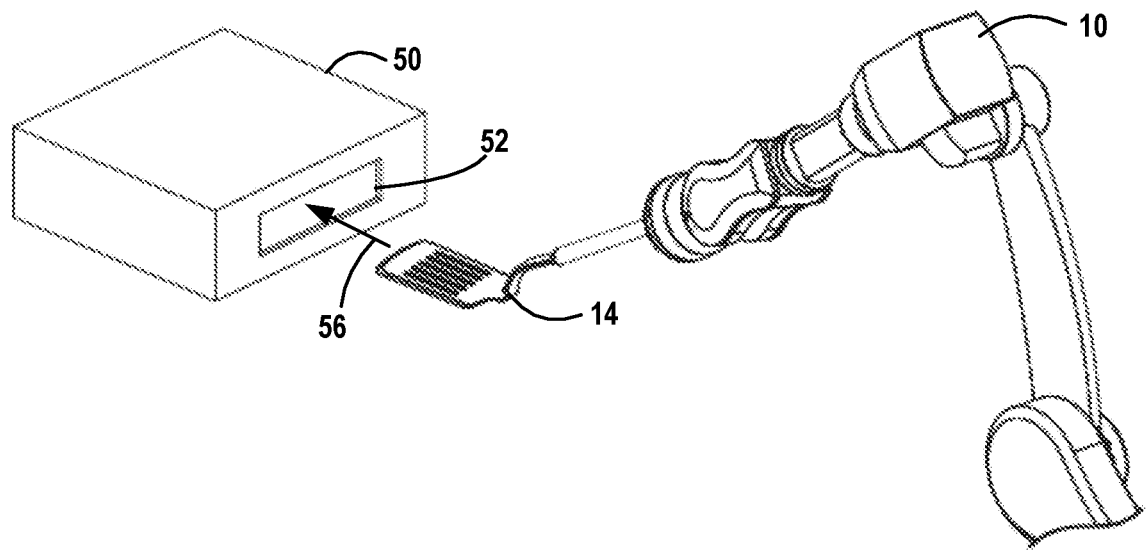
FIG. 3 is a diagram illustrating the example automated food service robot of FIGS. 1-2 in a first sanitization position with respect to the antimicrobial lighting fixture in accordance with the present disclosure.
Figure 4:
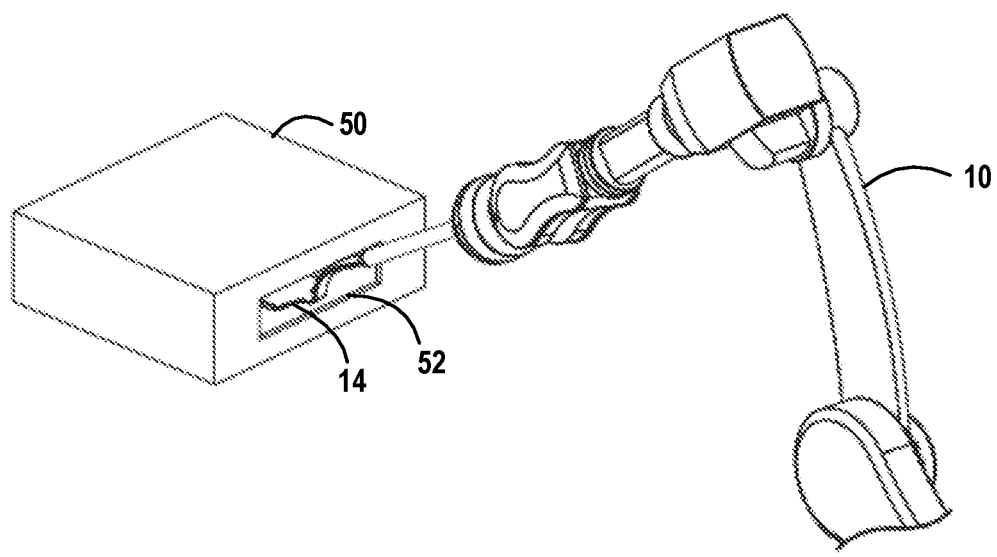
FIG. 4 is a diagram illustrating the example automated food service robot of FIGS. 1-3 in a second sanitization position with respect to the antimicrobial lighting fixture in accordance with the present disclosure.

FIG. 3 is a diagram illustrating the example automated food service robot 10 of FIGS. 1-2 in a first example sanitization position with respect to the example antimicrobial lighting fixture 50 in accordance with the present disclosure. FIG. 4 is a diagram illustrating the example automated food service robot 10 of FIGS. 1-3 in a second example sanitization position with respect to the example antimicrobial lighting fixture 50 in accordance with the present disclosure.

Food service robot 10 may operate in a food preparation or food prep mode, such as shown in FIG. 1, in which food service robot handles and/or prepares food. Food service robot 10 may also operate in a sanitization mode, such as shown in FIGS. 3 and 4, in which it automatically subjects one or more food contact surfaces and/or other surfaces to be sanitized to antimicrobial light within the sanitization chamber 52 of antimicrobial lighting fixture 50. Based on detection of one or more conditions, automated food service robot 10 will exit the food prep mode and enter the sanitization mode. While in the sanitization mode, food service robot 10 automatically executes a sanitization procedure. For example, to execute a sanitization procedure, food service robot 10 may move from a food prep position (such as that shown in FIG. 1 or any other position in which the food service robot may handle and/or prepare food) to a first sanitization position, such as that shown in FIG. 3. In the first sanitization position, food service robot 10 senses its position relative to enclosure 58 and/or opening 52 such that utensil attachment 14 is aligned with opening 52. To do this, food service robot 10 and/or antimicrobial lighting fixture 50 may include one or more sensors configured to detect the relative position of food service robot 10 with respect to enclosure 58 and/or slot 52.

Food service robot 10 may then move in the direction indicated by arrow 56 from the first sanitization position as shown in FIG. 3 to the second sanitization position as shown in FIG. 4. In the second sanitization position, utensil attachment 14 is positioned within the chamber formed by enclosure 58 such that all food contact surfaces to be sanitized during the current sanitization procedure may be exposed to antimicrobial light within the chamber 52.

In other examples, lighting fixture 50 may move with respect to food service robot 10 such that the target food contact or other non-food contact target surfaces are positioned within the sanitization chamber. It shall be understood therefore, that although FIGS. 3 and 4 illustrate a moveable food service robot 10 that moves with respect to a stationary lighting fixture 50, that one or both of food service robot and/or lighting fixture 50 may be moveable (either manually or automatically) such that the target food contact or non-food contact surfaces of a food service robot may be subjected to antimicrobial irradiation within the sanitization chamber, and that the disclosure is not limited in this respect.

Figure 5:
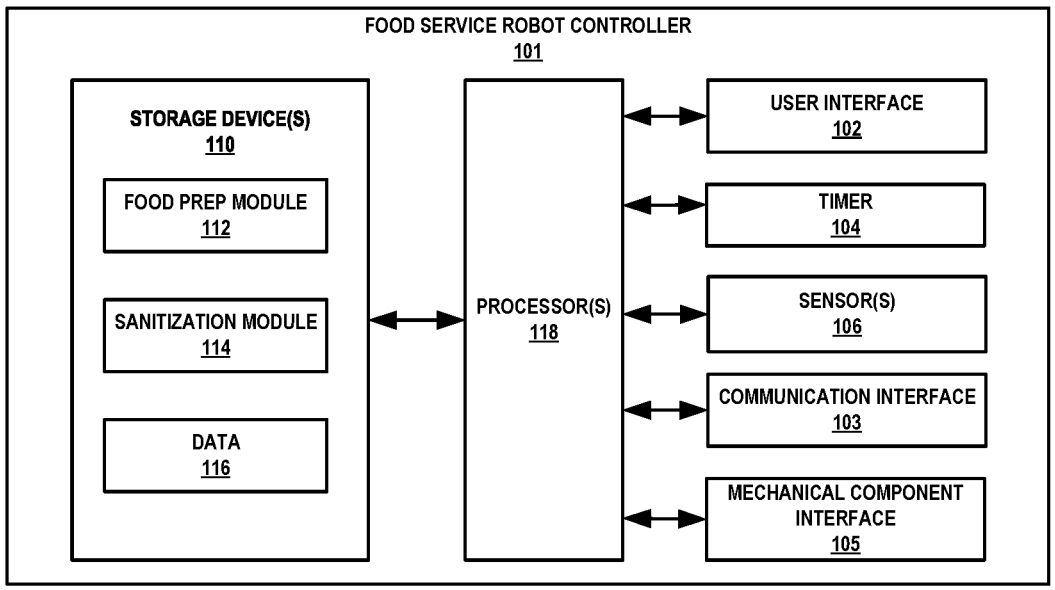
FIG. 5 is a block diagram of the electronic components of an example automated food service robot programmed to subject one or more food contact surfaces to an antimicrobial lighting fixture in accordance with the present disclosure.

FIG. 5 is a block diagram showing the electronic components of an example automated food service robot 100 configured to automatically subject one or more target food contact surfaces and/or non-food contact surfaces to a sanitization procedure by an antimicrobial lighting fixture in accordance with the present disclosure. Food service robot 100 includes a controller 101, a user interface 102, a mechanical component interface 105, a communication interface 103, one or more timer(s) 104, and one or more sensor(s) 106.

Mechanical component interface 105 provides for electronic communication of control signals and/or status information between controller 101 and the mechanical components of the food service robot 100. Communication interface 103 provides for wired or wireless communication between controller 101 and one or more external computing devices, such as an antimicrobial light array controller and/or one or more local or remote computing device(s), through wired or wireless connections or network(s). For example, through communication interface 103, food service robot controller 101 may transmit data concerning food preparation activities and/or sanitization procedures executed by the food service robot to one or more local or remote computing device(s). The data may be stored at the one or more local or remote computing devices, and reports may be generated concerning the food preparation activities and/or sanitization procedures executed by the food service robot. This may permit a user, such as a supervisor or manager of a food establishment, to view reports concerning food preparation and/or sanitization procedures executed by one or more food service robots in use at the establishment, generate reports for purposes of food safety inspections, review food preparation and/or sanitization procedure data for benchmarking purposes, generate notifications to service technicians in the event that one or more antimicrobial lighting elements need to be replaced, and the like. The notifications may be any form of electronic communication, including but not limited to emails, text messages, instant messages, voice mails, etc. The local or remote computing devices may be any form of computing device, including but not limited to desktop computers, laptop computers, tablet computers, mobile devices, smart phones, personal digital assistants, server computing devices, etc.

Controller 101 includes one or more processor(s) 118 and one or more storage device(s) 110. Storage device(s) 110 includes a food prep module 112, a sanitization module 114 and data storage 116. Food prep module 112 and sanitization module 114 may perform operations described using software, hardware, firmware, or a mixture of hardware, software, and firmware residing in and/or executed by controller 100. Controller 100 may execute modules 112 and 114 with one or more processors 118. Controller 100 may execute modules 112 and 114 as a virtual machine executing on underlying hardware. Modules 112 and 114 may execute as a service or component of an operating system or computing platform. Modules 112 and 114 may execute as one or more executable programs at an application layer of a computing platform. User interface 102 and modules 112 and 114 may be otherwise arranged remotely to and remotely accessible to controller 100, for instance, as one or more network services operating at a network in a network cloud.

Food prep module 112 and sanitization module 114 includes instructions that are executable by processor(s) 118 to cause the food service robot to perform one or more tasks. For example, food prep module 112 includes instructions that are executable by processor(s) 118 to automatically control the mechanical components of food service robot 100 to carry out one or more food handling or preparation tasks. As another example, sanitization module 114 includes instructions that are executable by processor(s) 118 to automatically control the mechanical components of food service robot 100 to carry out one or more food contact surface sanitization procedures in accordance with the present disclosure.

Food prep module 112 may analyze information received from one or more sensor(s) 106 to automatically control the mechanical components of the food service robot 100 (such as robotic arm shown in FIGS. 1 and 3-4) to perform one or more food handling or preparation tasks. For example, food prep module 112 may analyze information from one or more sensor(s) 106 to understand the food preparation environment, determine position of the mechanical components with respect to the food preparation environment and/or the food, control movements of the mechanical components to carry out food handling and processing tasks, etc. Sensor(s) 106 may include, for example, one or more cameras (visible, RGB, IR, etc.), image capture devices, proximity sensors, optical sensors, magnetic sensors, motion detectors, range sensors, and any other sensor type that can be used to provide information concerning the food preparation environment and the food service robot's location or position with respect to the environment and/or the food. Sensor(s) 106 may also include one or more sensors for detecting the intensity of antimicrobial light during a sanitization procedure.

Sanitization module 114 may analyze information received from one or more sensor(s) 106 to automatically control the mechanical components of the food service robot 100 (such as robotic arm shown in FIGS. 1 and 3-4) to perform a sanitization procedure. For example, sanitization module 114 may analyze information from one or more sensor(s) to determine a position of the mechanical components with respect to an antimicrobial lighting fixture and to control movements of the mechanical components to subject one or more food contact surfaces and/or one or more non-food contact surfaces to an antimicrobial light treatment by the antimicrobial lighting fixture.

Food prep module 112 may further include instructions that are executable by processor(s) 118 to cause the food service robot 100 to determine when it should initiate a sanitization procedure. For example, food prep module 112 may further include instructions that are executable by processor(s) 118 to cause the food service robot 100 to, based on detection of one or more conditions, exit a food prep mode and enter a sanitization mode. The one or more conditions may include a food type, a food prep status, a predetermined period of time, a kitchen event (such as a spill or other kitchen incident that may suggest that a sanitization procedure should be performed), a food service robot status, a kitchen equipment status, a communication from a piece of kitchen equipment, a communication from another computing device, and the like.

Sanitization module 114 may further include instructions that are executable by processor(s) 118 to cause the food service robot 100 to determine when a sanitization procedure is complete. For example, sanitization module 112 may further include instructions that are executable by processor(s) 118 to cause the food service robot 100 to, based on detection of one or more conditions, exit a sanitization mode and enter a food prep mode. The one or more conditions may include a food type, a food prep status, a predetermined period of time, a antimicrobial light dosage, an amount or intensity of antimicrobial light detected by one or more sensors, a food service robot status, a kitchen equipment status, a communication received from an antimicrobial light fixture, a communication received from another computing device, etc.

Figure 6:
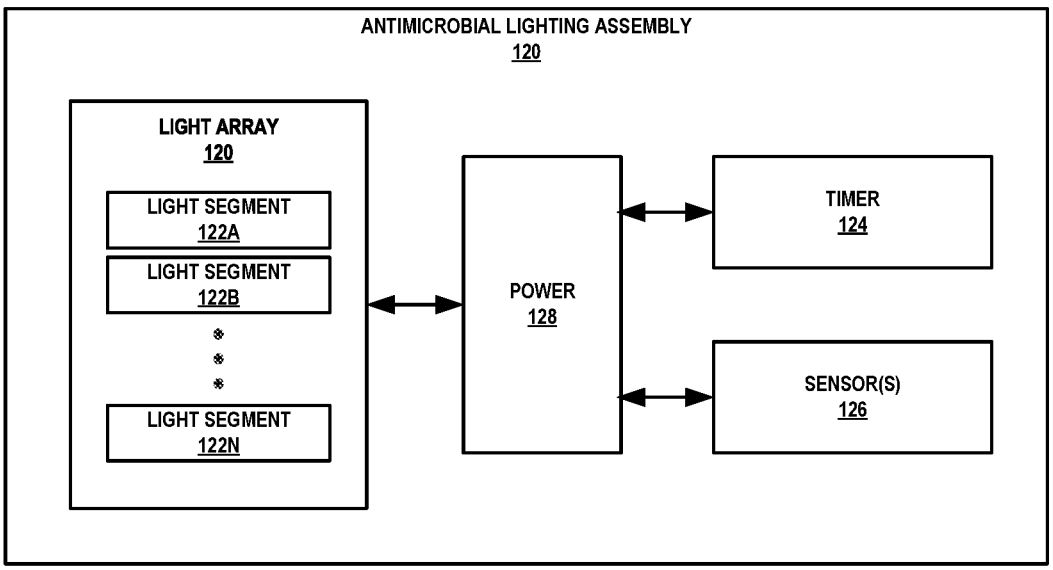
FIG. 6 is a block diagram of the electronic components of an example antimicrobial lighting fixture including an antimicrobial light array in accordance with the present disclosure.

FIG. 6 is a block diagram showing the electronic components of an example antimicrobial lighting fixture assembly 120 including an antimicrobial light array 120 in accordance with the present disclosure. Antimicrobial light array 120 includes one or more individually controllable antimicrobial light segments 122A-122N. Antimicrobial lighting assembly 120 also includes a power module 128, a timer 124 and one or more sensor(s) 126. Power module 128 is configured to provide power to light array 120. Timer 124 provides time of day information to the power module 128. Sensor(s) 126 detect presence and/or relative position of at least a portion of a food service robot with respect to the enclosure of the antimicrobial lighting fixture and thus to antimicrobial light array 120. For example, sensor(s) 126 may detect one or more of presence of at least a portion of a food service robot in proximity to an entrance to an antimicrobial chamber of the antimicrobial lighting fixture, movement of least a portion of a food service robot through the entrance to the antimicrobial chamber, the relative position of one or more food contact surfaces of the food service robot within the antimicrobial chamber, or any other positional information of the food service robot with respect to the antimicrobial lighting fixture. Sensor(s) 126 may further include a meter to verify antimicrobial light effectiveness and alert when the light source(s) need maintenance or replacement.

In this example system, power to the light array 120 may be controlled based on time of day, based on detected presence (or absence) of a target surface in or near the antimicrobial lighting fixture, or may be based on actual usage of the automated food service robot. For example, light array 120 may be controlled based on presence information received from sensor(s) 126. For example, sensor(s) 126 may include one or more motion sensors that detect presence of at least a portion of an automated food service robot, and the light array 120 may enable or disable one or more of the antimicrobial light segments 122A-122N based on this detected presence information. In another example, timer 124 may provide time of day information and light array 120 may enable or disable one or more of the antimicrobial light segments 122A-122N based on time of day information. In another example, antimicrobial lighting system 100 may receive actual food service robot usage information from a controller associated with the food service robot, and light array 120 may enable or disable one or more of the antimicrobial light segments 122A-122N based on receipt of the usage information.

Light array 120 is controlled such that each identified food contact surface of an automated food service robot that is placed within the antimicrobial chamber is illuminated with light of an antimicrobial wavelength at a sufficient dosage to effect microbial inactivation on identified food contact surfaces. The dosage may be defined as the irradiance, or the power received by a surface per unit area (e.g., as measured in watts per square centimeter, $W/cm^2$) of the antimicrobial wavelength(s) measured at the target surface. The irradiance is dependent at least in part by the power applied to the light source(s), the distance from the light source to the target area, the total surface area illuminated, and the time of exposure.

In some examples, it is not necessary to continuously illuminate all target food contact surfaces at the same time or at the same dose. Food contact surfaces can be treated automatically and selectively by the antimicrobial light when, for example, the treatment is determined to be most effective, based on usage information, time of day information, or on a periodic basis, etc.

The antimicrobial light treatment protocol may include a high exposure setting (full power on or highest intensity) antimicrobial cycle mode that occurs when usage of the automated food service robot is predicted to be in an unused state (at night, or during closing times, for example) as well as a treatment interrupt mode (power down) for power savings during low usage or unused times. In other examples, a high exposure setting may be used during high usage times when shorter downtimes of the food service robot may be desired. The antimicrobial light treatment protocol may also include a reduced power mode or modified setting in which certain antimicrobial light segments are selectively controlled to output a reduced intensity, but at a level that is sufficient to inactivate one or more microorganisms at the target surface(s). The individual light segments 122A-122B may thus be individually and selectively controlled to provide antimicrobial irradiation at one or more intensity settings and at various times throughout the day to ensure sufficient antimicrobial inactivation at the target food contact surfaces.

In some examples, control of the settings may be determined based on the time of day. For example, lighting array 120 may be controlled based on time and date information from timer 124 to determine whether the current time corresponds to a heavy usage time of the food service robot or to a reduced or standby usage time of the food service robot. In a restaurant application, for example, a heavy usage time for an automated food service robot may correspond to the hours around mealtimes, such as breakfast, lunch, and/or dinner, while a reduced usage time may correspond to nighttime hours or other times when the restaurant is closed. Light array 120 may therefore determine the time and date from information received from timer 124 and individually control activation of selected antimicrobial light segments 122A-122N based on the time and date. For example, light array 120 may activate all antimicrobial light segments 122A-122N at a maximum setting and for a relatively longer period of time upon determining that the time and date correspond to a time when the automated food service robot typically experiences a reduced or no usage level (such as when a restaurant is closed). Array control module 212 may activate selected antimicrobial light segments 122A-122N at a maximum setting and for a relatively shorter period of time upon determining that the time and date correspond to a time when the automated food service robot typically experiences relatively higher usage levels and/or maximum usage levels. This may help to ensure such that sufficient sanitization of food contact surfaces can be achieved in a relatively shorter period of time to minimize impact on the food preparation processes during high usage times.

It shall be understood that antimicrobial light arrays including one or more antimicrobial light segments may be adapted for antimicrobial irradiation of any automated food service robot surface. For example, the antimicrobial light segments 122A-122N may include individual light elements, straight line segments, flexible LED light strips, curved light segments, or flexible segments that may be bent or curved to fit within any desired enclosure shape and/or to provide the desired antimicrobial light intensity distribution within the volume of the antimicrobial chamber.

Each light segment 122A-122N includes one or more individual antimicrobial light sources. In some examples, one or more of antimicrobial light segments 122A-122N may be implemented using a commercially available LED light strip having a peak wavelength of about 405±5 nm, such as the Single Color Outdoor Weatherproof LED Flexible Light Strip, wavelength 405 nm, Part Number WFLS-UV30, available from Super Bright LEDs Inc., of St. Louis, Missouri, USA (www.superbrightleds.com). However, it shall be understood that any commercially available or custom designed light segment may be used, and that the disclosure is not limited in this respect. In other examples, one or more of the antimicrobial light segments 122A-122N may be implemented using one or more commercially available UV-C lamps emitting wavelengths in a range of 254±5 nm (i.e., from about 249-259 nm)

Each antimicrobial light segment 122A-122N may be individually controllable such that they may be activated and/or deactivated independently of one another. Each of the antimicrobial light segments 122A-122N, either alone or in combination with one or more of the other antimicrobial light segments 122A-122N, emits antimicrobial light at a wavelength and irradiance sufficient to inactivate one or more microorganisms on the food contact surfaces of the automated food service robot. For example, antimicrobial light segments 122A-122N may include one or more elements that emit light at a wavelength of about 405±15 nm and at a sufficient irradiance to achieve sufficient levels of microorganism inactivate at the target food contact surface(s). Use of multiple customizable and individually controllable antimicrobial light segments allows for controlled distribution of antimicrobial irradiation to achieve microbial inactivation across the target food contact surfaces of an automated food service robot.

Figure 7:
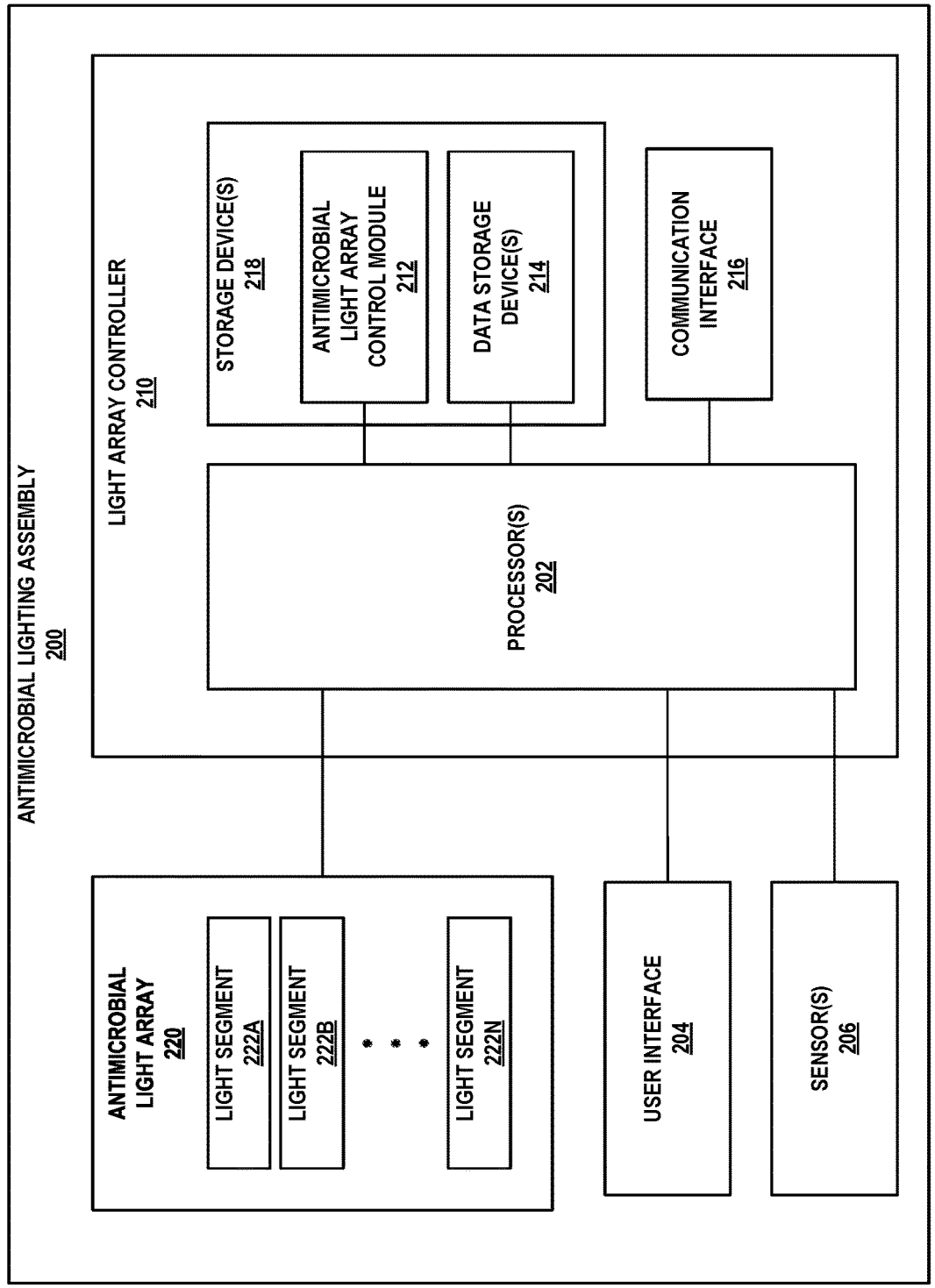
FIG. 7 is a block diagram of the electronic components of another example antimicrobial lighting fixture including an antimicrobial light array in accordance with the present disclosure.

FIG. 7 is a block diagram of the electronic components of another example sanitization lighting assembly 200 including one or more antimicrobial lighting elements for microbial inactivation of one or more food contact surfaces (and/or one or more non-food contact surfaces) of an automated food service robot in accordance with the present disclosure. Assembly 200 includes an antimicrobial light array 220 including one or more antimicrobial light segments 222A-222N, one or more sensor(s) 206, a user interface 204, and a light array controller 210. Light array controller 210 includes one or more processors 202, and storage devices including a light array control module 212, data storage 214, and communication interface(s) 216.

In order to provide varying intensities of antimicrobial irradiation within the antimicrobial chamber, the one or more antimicrobial lighting segments 222A-222N in antimicrobial lighting array 220 may be individually controllable. For example, to provide relatively higher intensity antimicrobial lighting, lighting segments 222A-222N may be individually controlled to provide such higher intensity antimicrobial lighting at one or more predetermined times or upon detection of one or more events.

One such event may include detection of presence of an automated food service robot. Sensor(s) 206 may include one or more of device that detects the distance, presence, or absence of an automated food service robot near the entrance to the antimicrobial chamber and/or within the antimicrobial chamber. Sensor(s) 206 may further include a meter to verify antimicrobial light effectiveness, and controller 210 may generate an alert or notification when the sensed intensity of the light emitted by light source(s) indicate that maintenance or replacement of one or more lighting elements is needed.

In some examples, antimicrobial light segments 222A-22N may be controlled to emit antimicrobial light in a first wavelength range within the interior of the sanitization chamber so as to achieve adequate sanitization of food contact surfaces in a relatively shorter period of time (e.g., exposure time of seconds to a few minutes). In another example, antimicrobial light segments 222A-22N may be controlled to emit antimicrobial light in a second wavelength range to achieve sanitization of food contact surfaces over a longer period of time (e.g., exposure time of several minutes to a few hours). For example, the first wavelength range may include UV light having one or more wavelengths in a range of about 254±5 nm, and the second wavelength range may include light having one or more wavelengths in a range of about 405±15 nm.

The first wavelength range may be useful for those applications or times of day when the food service robot is busy preparing food and relatively short sanitization times are desired to minimize downtime of the food service robot. The second wavelength range may be useful during times of less usage, such as during the night or during times when a food establishment is closed. The second wavelength range may also be useful to limit human exposure to ultraviolet light, as light in the second wavelength range is generally considered safer for human exposure than the first wavelength range. In other examples, both the first and/or the second wavelength ranges may be emitted simultaneously or in a predetermined sequence during a sanitization procedure.

Communication interface(s) 216 may include any type of interface(s) that permit wired or wireless communication between controller 210 and any other local and/or remote computing devices. For example, communication interface(s) 216 may permit communication between controller 210 and the controller of an automated food service robot, such as controller 100 as shown in FIG. 5. Communication interface(s) 216 may also provide for wired or wireless communication between controller 210 and one or more external computing devices, such as one or more local or remote computing device(s), through wired or wireless connections or network(s). For example, through communication interface 215, antimicrobial lighting assembly controller 200 may transmit data concerning sanitization procedures executed by the antimicrobial light assembly to one or more local or remote computing device(s). The data may be stored in data storage device(s) 214 and/or at the one or more local or remote computing devices, and reports may be generated concerning the sanitization procedures executed by the antimicrobial lighting assembly. The reports may be generated by the light array controller 210 under control of antimicrobial light array control module 212 and/or they may be generated by the local or remote computing device(s). This may permit a user, such as a supervisor or manager of a food establishment, to view reports concerning sanitization procedures executed by one or more food service robots in use at the establishment, generate reports for purposes of food safety inspections, review food preparation and/or sanitization procedure data for benchmarking purposes, generate notifications to service technicians in the event that one or more antimicrobial lighting elements need to be replaced, and the like. The notifications may be any form of electronic communication, including but not limited to emails, text messages, instant messages, voice mails, etc. The local or remote computing devices may be any form of computing device, including but not limited to desktop computers, laptop computers, tablet computers, mobile devices, smart phones, personal digital assistants, server computing devices, etc.

Antimicrobial light array control module 212 includes computer readable instructions configured to be executed on the one or more processors 202 to enable controller 210 to control activation of antimicrobial light segments 222A-222N of light array 220. For example, array control module 212 may enable controller 210 to individually control activation of antimicrobial light segments 222A-222N based on the information received from sensor(s) 206 and/or based on information received from or associated with a food service robot. For example, array control module 212 may enable controller 210 to individually control activation of antimicrobial light segments 222A-222N based on the food prep information received from or associated with a food service robot to be sanitized. The food prep information may include, for example, the application and/or the environment in which antimicrobial lighting fixture is to be used, the type of food service robot and/or food contact surfaces to be sanitized, the type of food to be handled and/or prepared, the usage patterns for the food service robot, the time of day, integration of the automated food service robot sanitization procedures with manual cleaning and sanitization protocols, and other factors. Thus, it shall be understood that antimicrobial light array control module may be programmed to control antimicrobial light array and antimicrobial light array segments in a very flexible manner so as to be customized to the particular environment in which the food service robot is to be used.

For example, antimicrobial light array control module 212 may include instructions that, when executed by processor(s) 202, allow controller 210 to individually control the light segments 222A-222N. Control of the light segments may be based on, for example, a predetermined sanitization procedure, information received from a food service robot to be sanitized, a time of day, and other factors as described herein.

Figure 8:
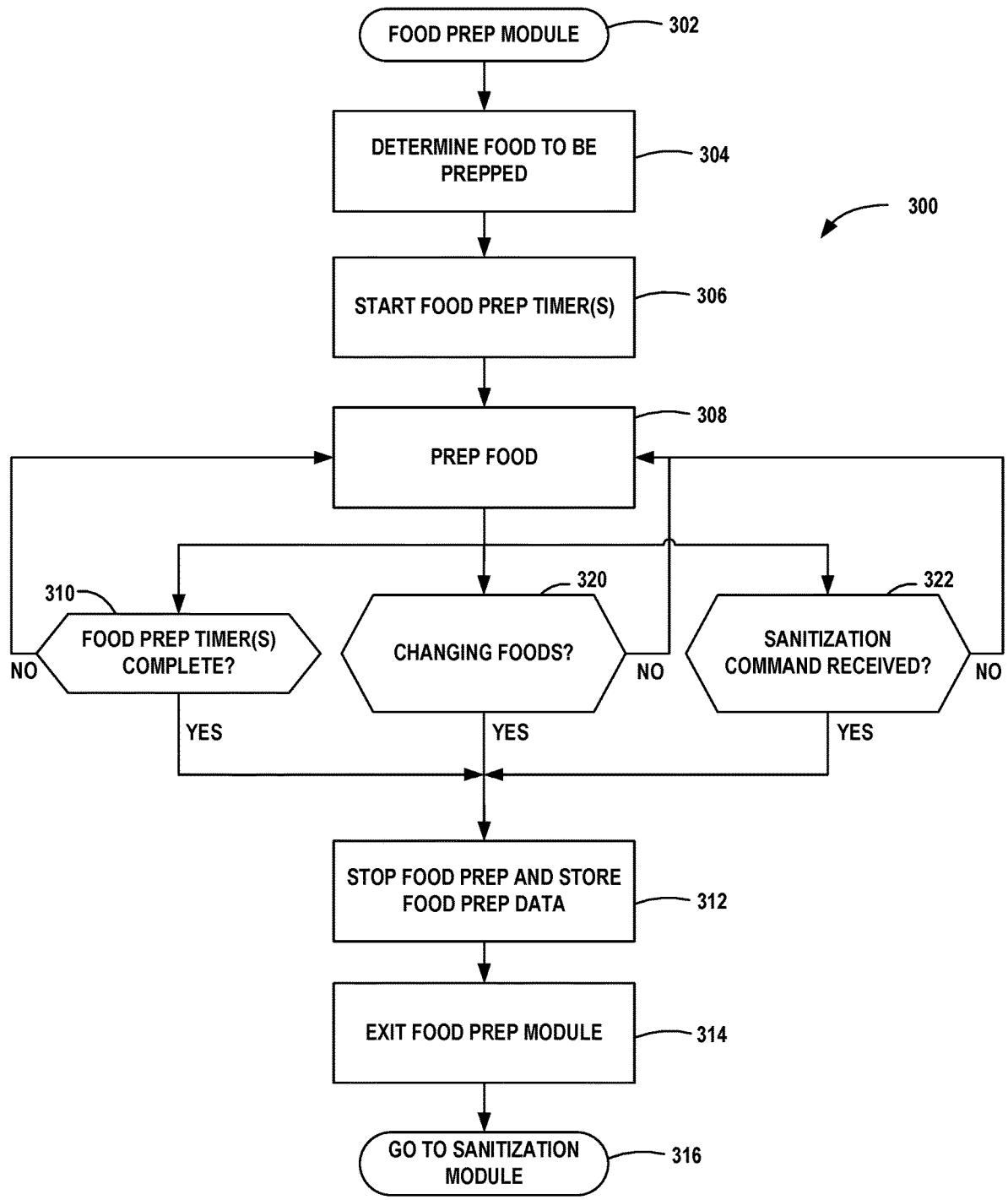
FIG. 8 is a flow chart showing an example process by which an automated food service robot may determine when to initiate a sanitization event in accordance with the present disclosure.

FIG. 8 is a flow chart showing an example process (300) by which a computing device (such as controller 101 of an automated food service robot as shown in FIG. 5) may control a food preparation process and determine when to initiate a sanitization event in accordance with the present disclosure. During execution of the process (300), automated food service robot may be considered to be in a food preparation mode or food prep mode. The process (300) may be stored in one or more storage device(s), such as food prep module 112 stored in storage device(s) 110, and executed by one or more processor(s), such as processors 118 of food service robot controller 101 as shown in FIG. 5.

At the start of a food preparation process (302), the computing device determines the type of food to be prepared (304). The computing device may also start one or more food preparation timers (306). In some examples, the type of food to be prepared may be a factor in determining how often the food service robot should perform a sanitization procedure. In some applications, for example, it may be desirable for the food service robot to perform a sanitization procedure more often when preparing meats than when preparing vegetables. The one or more food preparation timer(s) track the amount of time that the food service robot has been in a food prep mode. The food service robot may perform a sanitization procedure when one or more of the food preparation timer(s) reach a predetermined amount of time. For example, a food preparation timer may be set to a predetermined minimum frequency at which sanitization procedures should be performed. The 2017 FDA Food Code, for example, states that food contact surfaces and utensils shall be cleaned throughout the day at least every 4 hours. In addition or alternatively, a food establishment may set one or more other specified minimum frequencies at which a food service robot should perform a sanitization procedure. As another example, the one or more food preparation timer(s) may be based on the type of food to be prepared. For example, a food preparation timer for preparing meats or other higher risk foods may be of a shorter duration than a food preparation timer for preparing vegetables or other lower risk foods. In other examples, the one or more food preparation timers may be customizable depending upon the application and/or by the customer. Thus, in some examples, there may be more than one food preparation timer (306) at any given time.

Based on the type of food to be prepared (304), the computing device controls preparation of the food (308). For example, preparation of the food may be controlled by execution of food prep module 112 by food service robot controller 101. In such examples, a food service robot controller 101 may control one or more mechanical components of a food service robot during the food preparation process by sending and receiving control signals through a mechanical component interface 105 as shown in FIG. 5. Control of the mechanical components of the food service robot (such as robotic arm shown in FIGS. 1 and 3-4) may be accomplished based on analysis of information received from one or more sensor(s) (such as sensor(s) 106 as shown in FIG. 5) to automatically control the mechanical components of the food service robot to perform one or more food handling or preparation tasks. For example, the computing device may analyze information from one or more sensor(s) to understand the food preparation environment, determine position of the mechanical components with respect to the food preparation environment and/or the food, control movements of the mechanical components to carry out food handling and processing tasks, etc. The sensor(s) may include, for example, one or more cameras (visible, RGB, IR, etc.), image capture devices, proximity sensors, optical sensors, magnetic sensors, motion detectors, range sensors, and any other sensor type that can be used to provide information concerning the food preparation environment and the food service robot's location or position with respect to the environment and/or the food.

In some examples, there may be several conditions which determine when a food service robot should perform a sanitization procedure. Some of these example conditions are shown in FIG. 8. These conditions may include a determination that one or more food preparation timers are complete (310), a determination that the food service robot is changing a type of food to be prepared (320), and/or receipt of a manual or remotely generated sanitization command (322).

As discussed above, food service robot starts one or more food preparation timer(s) (306) to monitor the length of time that food service robot has been preparing food, and/or to monitor when a predetermined amount of time has elapsed at which a food service robot should perform a sanitization procedure. When computing device determines that one or more of the food preparation timers are complete (310), this means that the food service robot has been preparing food for a predetermined amount of time corresponding to the food preparation timer, and that the food service robot should execute a sanitization procedure. Each food preparation timer may count up to a predetermined amount of time, they may start at a predetermined amount of time and count down to zero, or monitor the predetermined amount of time in any other way, and it shall be understood that the disclosure is not limited in this respect. When the computing device determines that one or more food preparation timer(s) are complete (310), the computing device controls the mechanical components of the food service robot to stop the food preparation procedure (312), exit the food prep module (314) and enter a sanitization module (316). The sanitization procedure may then be executed before the food service robot returns to a food prep mode to continue an existing food preparation procedure or to start a new food preparation procedure.

In some examples, a food service robot may stop preparing one food in order to start preparing a different food. In such examples, food service robot should execute a sanitization procedure before starting preparation of the new food to reduce the risk of cross-contamination. In such examples, a computing device, such as a controller of a food service robot, may determine that a change in the food being prepared is to occur (320). The computing device may then control the mechanical components of the food service robot to stop the food preparation procedure (312), exit the food prep module (314) and enter a sanitization module (316). The sanitization procedure may then be executed before the food service robot returns to a food prep mode to begin a new food preparation procedure corresponding to preparation of the new food.

In other examples, a sanitization procedure may be initiated on-demand. For example, a user may determine, for whatever reason, that a food service robot should perform a sanitization procedure. The user may include, for example, a local employee or manager of the food establishment, or a remotely located employee or manager of the food establishment. In some examples, a user may manually initiate a sanitization procedure by entering a sanitization command through a user interface of the food service robot, such as user interface 102 as shown in FIG. 5. For example, a user may manually initiate a sanitization procedure through a touch screen, keyboard, mouse, or other input device of a user interface. In other examples, a user may remotely initiate a sanitization procedure by transmitting a sanitization command to the food service robot controller from a remote computing device, and which is received through a communication interface, such as communication interface 103 as shown in FIG. 5. If the computing device, such as a controller of a food service robot, receives a manual or remote sanitization command (322), the computing device may then control the mechanical components of the food service robot to stop the food preparation procedure (312), exit the food prep module (314) and enter a sanitization module (316). The sanitization procedure may then be executed as shown in FIG. 9.

Before leaving the food preparation procedure and starting a sanitization procedure, a computing device, such as a controller of a food service robot, stores food preparation data associated with the food preparation procedure (312). For example, the food preparation data may include one or more of a time and date stamp, one or more type(s) of food prepared, utensils used, food service robot identification information, a record of food preparation actions performed, data concerning the number of food items prepared, and any other information relevant to the food preparation procedure. The food preparation data may be stored in, for example, data storage device 116 as shown in FIG. 5. The food preparation data may be stored and transmitted periodically or on-demand to one or more local or remote computing devices. This data may be used to generate one or more reports for management or other employees of a food establishment and/or to create reports for inspection purposes.

In some examples, before executing a sanitization procedure and/or at one or more times during the food preparation procedure, a food service robot may undergo a cleaning procedure. During a cleaning procedure, food residue, dirt and other soil accumulations are removed from the food contact or other surfaces of the food service robot. A cleaning procedure may be performed manually by one or more employees of a food establishment, and/or may be performed partially or fully automatically by one or more cleaning machines. In a fully automatic example, a food service robot may subject itself to cleaning procedure performed by an automatic clean-in-place cleaning machine before subjecting itself to a sanitization procedure.

Figure 9:
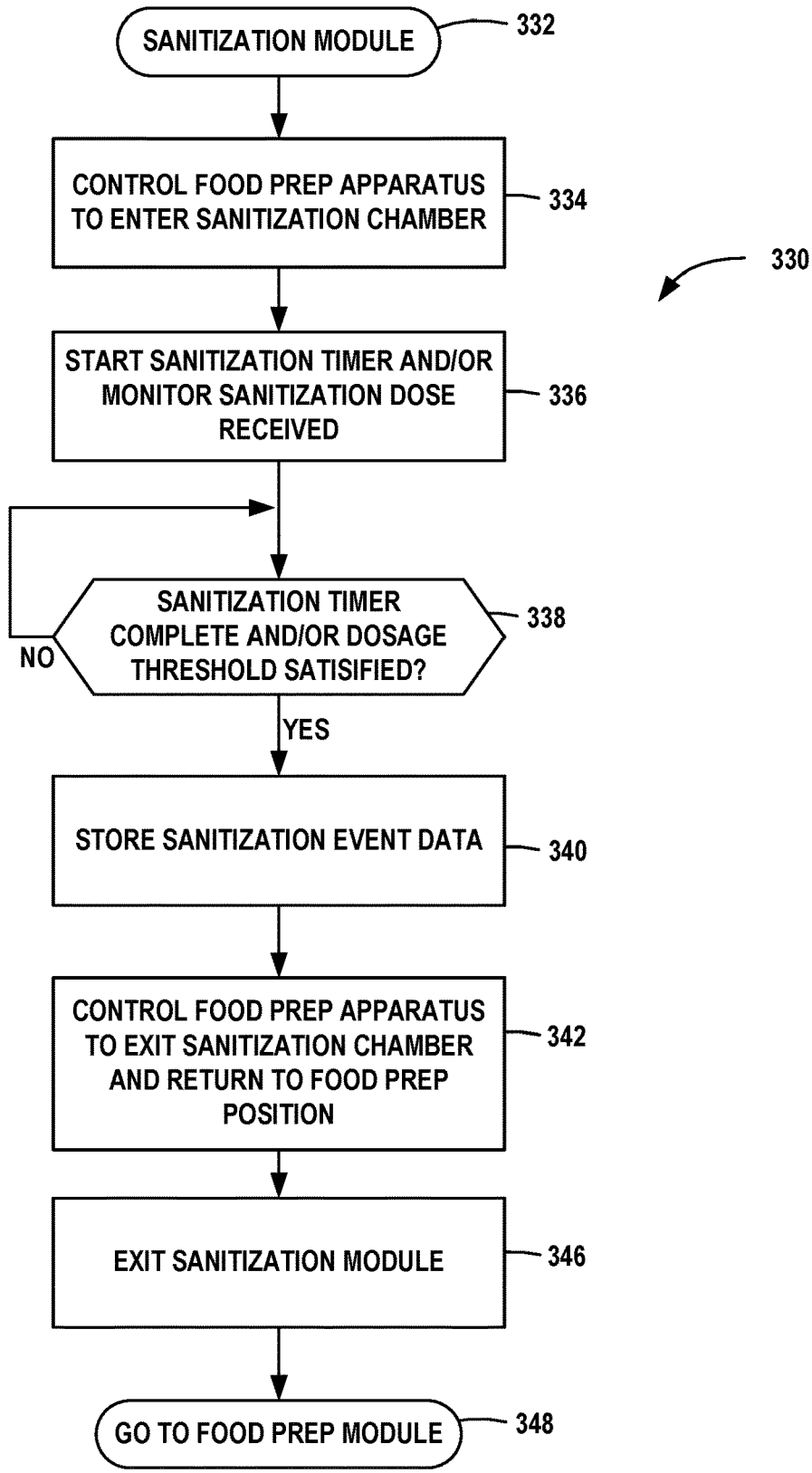
FIG. 9 is a flow chart showing an example process by which an automated food service robot may execute a sanitization event in accordance with the present disclosure.

FIG. 9 is a flow chart showing an example process (33) by which an automated food service robot may execute a sanitization procedure in accordance with the present disclosure. The process (330) may be stored in one or more storage device(s), such as sanitization module 114 stored in storage device(s) 110, and executed by one or more processor(s), such as processors 118, of food service robot controller 101 as shown in FIG. 5.

The computing device controls the mechanical components of food service robot such that one or more food contact surfaces enter a sanitization area (334). For example, a controller 101 as shown in FIG. 5 may execute instructions stored in sanitization module 114 to control one or more mechanical components (such as a robotic arm 10 as shown in FIGS. 1 and 3-4) such that one or more target food contact surfaces (such as at least a portion of utensil attachment 14) enters sanitization chamber 50 as shown in FIGS. 3 and 4. This may include controlling the mechanical components of the food service robot to move from a food preparation position (such as any position in which the food service robot is in a position to prepare food, such as shown in FIG. 1) to a first sanitization position with respect to an antimicrobial lighting fixture (such as shown in FIG. 3) and then to a second sanitization position with respect to the antimicrobial lighting fixture (such as shown in FIG. 4) in which the one or more target food contact surfaces are in position to be exposed to sanitization light by the antimicrobial lighting fixture.

In other examples, the sanitization chamber may be moved with respect to the food service robot to perform the sanitization procedure, or both the food service robot and the sanitization chamber may move relative to each other to perform the sanitization procedure. Thus, although the present disclosure describes an example in which the food service robot is moveable and the sanitization chamber does not move, it shall be understood that this description is for example purposes only, and that the disclosure is not limited in this respect.

Once the food service robot is in position within the sanitization chamber (332), the food service robot needs to determine when the sanitization procedure is complete. This may be accomplished in several different ways. For example, computing device of a food service robot may keep track of the length of time that it is subjected to the antimicrobial light within the sanitization chamber. To that end, computing device of a food service robot may start a sanitization timer (336). The sanitization timer determines the length of time the one or more target food contact surfaces are exposed to antimicrobial light by the antimicrobial lighting fixture. In some examples, the antimicrobial lighting fixture includes one or more sensors which sense presence of a food service robot in the sanitization chamber, and the antimicrobial lighting fixture automatically activates one or more antimicrobial lighting elements within the sanitization chamber upon detection of presence of at least a portion of food service robot within the sanitization chamber. In other examples, a controller of a food service robot and a controller of an antimicrobial lighting fixture may communicate with each other (such as through communication interfaces 103 and 216, respectively, and the controller of the antimicrobial lighting fixture activates one or more antimicrobial lighting elements within the sanitization chamber based on the communication with the controller of the food service robot.

In addition, the food service robot may include one or more sensor(s), such as sensor(s) 106 as shown in FIG. 5, that detect antimicrobial light within the sanitization chamber, and the one or more timer(s) may start upon detection of the antimicrobial light. In another example, computing device may monitor a dosage of the antimicrobial light received by the food contact surfaces in the sanitization chamber (336).

When the sanitization timer is complete and/or when a threshold dosage of antimicrobial light has been received (338), the computing device may store sanitization event data associated with the sanitization procedure (340). For example, the computing device may store a date and time stamp corresponding to the start and/or end of the sanitization procedure, a duration of the sanitization procedure, an antimicrobial light intensity setting of the sanitization procedure, a measured intensity of the antimicrobial light applied during the sanitization procedure, a dosage of the antimicrobial light received during the sanitization procedure, a food type corresponding to the food preparation event, a utensil attachment type, and any other information that may be relevant to the sanitization procedure.

The computing device controls the mechanical components of food service robot such that the mechanical components exit the sanitization area and return to a food preparation position (342). For example, a controller 101 as shown in FIG. 5 may execute instructions stored in sanitization module 114 to control one or more mechanical components (such as a robotic arm 10 as shown in FIGS. 1 and 3-4) such that the one or more target food contact surfaces (such as at least a portion of utensil attachment 14) is removed from sanitization chamber 50 and returns to a food preparation position. This may include controlling the mechanical components of the food service robot to move from second sanitization position to first sanitization position, and then to a food preparation position (such as any position in which the food service robot is in a position to prepare food, such as shown in FIG. 1).

The computing device may then exit the sanitization module (346) and return to the food preparation module (348).

FIG. 10 is a flow chart showing an example process (360) by which a computing device of an antimicrobial lighting fixture may control a sanitization procedure in accordance with the present disclosure. The process (360) may be stored in one or more storage device(s), such as light control module 212 stored in storage device(s) 218, and executed by one or more processor(s), such as processors 202 of antimicrobial light array controller 210 as shown in FIG. 7.

The computing device may sense presence of at least a portion of a food service robot within the sanitization area (364). For example, one or more presence sensors associated with an antimicrobial lighting assembly, such as sensor(s) 206 as shown in FIG. 6, may sense presence of a portion of a robotic arm and/or utensil attachment within the sanitization chamber. In some examples, the computing device may further receive food preparation data (366). For example, the food preparation data may be received from the controller of a food service robot that is performing the current sanitization procedure, and the food prep data may include one or more of a time/date stamp of the food prep procedure, type of food, a type of utensil attachment, a time/date stamp of a previous sanitization procedure, and/or any other information relevant to determining the appropriate parameters for the current sanitization procedure.

Antimicrobial light fixture may determine the appropriate antimicrobial light treatment to deliver during the sanitization procedure based on the food prep data (368). For example, the food prep data may include information on the time of day, or the type of food prepared, which may be factors in determining the antimicrobial wavelengths and/or the intensity of the antimicrobial light to be delivered during the sanitization procedure. For example, the time of day and/or the relative busy-ness of the food establishment may determine the wavelengths and/or intensity of antimicrobial light treatment to be delivered. During busy times of day (e.g., when high volumes of food are being prepared and shorter downtimes are desired), an antimicrobial light treatment that achieves sufficient sanitization of the target food contact surfaces in a relatively short amount of time (e.g., seconds or minutes) may be desired as opposed to an antimicrobial light treatment that may require a longer amount of time (e.g., several minutes or hours) to achieve sufficient sanitization.

As another example, the type(s) of microorganisms associated with the type(s) of food being prepared may be a factor in determining the dosage of the antimicrobial light treatment to be delivered. The dosage may include the wavelengths and intensity of the antimicrobial light treatment to be delivered. For example, the types of microorganisms associated with preparation of raw meats may require different dosage of antimicrobial light than the types of microorganisms associated with preparation of raw fruits and vegetables and/or preparation of prepared foods.

Based on any of these or other examples of the food preparation data, a controller of a antimicrobial lighting fixture may determine the appropriate antimicrobial lighting treatment (e.g., the wavelengths and the dosage to be delivered) (368) and controls one or more of the antimicrobial lighting elements to deliver the determined antimicrobial lighting treatment (370). For example, a controller 210 such as that shown in FIG. 7 may control one or more light segments 222A-222N of an antimicrobial lighting array 220 based on the food prep data. The controller may control the intensity, the wavelength(s), the duration, and/or any other characteristic of the light emitted by the one or more light segments 222A-222N based on the food prep data.

In some examples, during the sanitization procedure, antimicrobial light fixture monitors one or more parameters during the sanitization procedure. For example, the computing device of the antimicrobial light fixture may include one or more sensors (such as sensors 206 as shown in FIG. 7) that continuously monitor the irradiance or optical power (energy per unit time) of the antimicrobial light delivered by the one or more antimicrobial lighting elements within the sanitization chamber (371). The monitored intensity may be compared to a lamp replacement threshold. Monitoring of the antimicrobial light emitted by the antimicrobial lighting elements helps to ensure effectiveness of the antimicrobial lighting treatment as the output of the antimicrobial lighting elements generally decreases over time. Monitoring of the effectiveness of the antimicrobial lighting elements may thus help to ensure that the food contact surfaces within the sanitization chamber receive the specified dosage to achieve sufficient inactivation of the target microorganisms. If the monitored intensity does not satisfy a predetermined threshold (372) the computing device may generate a lamp replacement notification (378). This may also include extending the period of time during which the antimicrobial light treatment is delivered to ensure that the specified dosage is received at the target surfaces.

The computing device may store and/or transmits sanitization event data corresponding to the sanitization event (380). For example, a controller such as controller 210 may store the sanitization event data in a data storage device 214 as shown in FIG. 7. In this example, the sanitization event data may include one or more of a time/date stamp of the sanitization procedure, food service robot identification information, some or all of the food prep data corresponding to the food service robot, antimicrobial lighting assembly identification information, the measured irradiance of the one or more antimicrobial lighting elements, the fact that a lamp replacement notification was generated, the dosage of antimicrobial light delivered, whether or not the specified dosage was delivered, and any other information relevant to the sanitization procedure. The sanitization event data may be transmitted, by communication interface 216 as shown in FIG. 7, for example, to one or more local or remote computing devices for review by employees or the food establishment or other users (376).

If the intensity satisfies the lamp replacement threshold, the computing device may monitor the dosage of the antimicrobial light received within the sanitization chamber during the sanitization procedure (373). For example, one or more sensors, such as one or more of sensor(s) 206 as shown in FIG. 7, may monitor the dosage of the antimicrobial light received within the sanitization chamber during the sanitization procedure.

When the specified dosage of antimicrobial light has been received (373), the computing device deactivates the one or more antimicrobial lighting elements (374) and stores sanitization event data (376). For example, a controller such as controller 210 may store the sanitization event data is a data storage device 214 as shown in FIG. 7. The sanitization event data may include one or more of a time/date stamp of the sanitization procedure, food service robot identification information, some or all of the food prep data corresponding to the food service robot, antimicrobial lighting assembly identification information, the measured irradiance of the one or more antimicrobial lighting elements, the dosage of antimicrobial light delivered, whether or not the specified dosage was delivered, and any other information relevant to the sanitization procedure. The sanitization event data may be transmitted, by communication interface 216 as shown in FIG. 7, for example, to one or more local or remote computing devices for review by employees or the food establishment or other users (376).

Although the examples presented herein are described with respect to automated food handling/preparation applications, it shall be understood that the techniques described herein may be applied to a variety of other applications. Such applications may include, for example, food and/or beverage processing, medical instrument processing, laundry applications, agricultural applications, hospitality applications, and/or any other application in which sanitizing of surfaces may be useful.

In one or more examples, the functions described herein may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some examples, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Additional Examples

EXAMPLE 1: A system comprising: an antimicrobial lighting fixture including: an enclosure forming a sanitization chamber; and one or more antimicrobial lighting segments, each antimicrobial lighting segment including one or more elements, wherein each element emits light within the sanitization chamber at a wavelength, irradiance, and direction sufficient to inactivate one or more microorganisms on a target surface within the sanitization chamber; and an automated food preparation apparatus including: at least one mechanical component controllable to prepare at least one food item and comprising at least one food contact surface; and a controller comprising computer readable instructions configured to be executed on one or more processors to control at least one mechanical component to move at least one food contact surface from a food preparation position to a sanitization position within the sanitization chamber.

EXAMPLE 2. The system of Example 1 wherein the antimicrobial lighting fixture controls each antimicrobial light segment based on food preparation information received from the automated food preparation apparatus.

EXAMPLE 3. The system of Example 1 wherein each of the one or more antimicrobial lighting segments are individually controllable by the antimicrobial lighting fixture.

EXAMPLE 4. The system of Example 1 wherein the antimicrobial lighting fixture further comprises a presence sensor that detects presence of at least a portion of the automated food preparation apparatus within the sanitization chamber.

EXAMPLE 5. The system of Example 1 wherein the antimicrobial lighting fixture further comprises one or more sensors that detect an intensity of antimicrobial light emitted within the sanitization chamber.

EXAMPLE 6. The system of Example 5 wherein the antimicrobial lighting fixture further includes a controller connected to receive the detected intensity of the antimicrobial light emitted within the sanitization chamber and that generates a lamp replacement notification when the detected intensity is below a threshold.

EXAMPLE 7. The system of Example 5 wherein the antimicrobial lighting fixture further includes a controller connected to receive the detected intensity of the antimicrobial light emitted within the sanitization chamber and that controls a duration of an antimicrobial light treatment received within the sanitization chamber by the at least one food contact surface of the automated food preparation apparatus based on the detected intensity.

EXAMPLE 8. The system of Example 1 wherein the automated food preparation apparatus includes a plurality of food contact surfaces, and wherein the one or more antimicrobial lighting segments are controllable to direct light at a wavelength and irradiance sufficient to inactivate one or more microorganisms on one or more of the plurality of food contact surfaces when the one or more food contact surfaces are present within the sanitization chamber.

EXAMPLE 9. The system of Example 1 wherein at least one of the antimicrobial lighting segments includes a plurality of light-emitting diode (LED) elements, and wherein each LED element emits light including wavelengths in a range of about 405±15 nanometers.

EXAMPLE 10. The system of Example 1 wherein at least one of the antimicrobial lighting segments includes one or more lighting elements that emit light in a short-wavelength ultraviolet (UV-C) wavelength range of 200-300 nm.

EXAMPLE 11. The system of Example wherein at least one of the antimicrobial lighting segments includes one or more elements that emits light including one or more wavelengths in a first wavelength range and at least one other of the antimicrobial lighting segments includes one or more elements that emit light including one or more wavelengths in a second wavelength range.

EXAMPLE 12. The system of Example 1 wherein the one or more microorganisms include at least one of *Bacillus* spp., *Pseudomonas* spp., *Listeria*, *Staphylococcus aureus*, *Salmonella* spp., *E. coli*, coliforms, *Legionella* spp., *Acinetobacter* species, *Candida* spp., *Saccharomyces* spp., *Aspergillus* spp., *Alcaligenes*, *Flavobacterium*, *Campylobacter* spp., *Clostridium perfringens, Clostridium botulinum, Shigella* spp., *Vibrio* spp., noroviruses, or hepatitis A.

EXAMPLE 13. A method comprising: controlling at least one mechanical component of a food preparation apparatus having at least one food contact surface to prepare at least one food item at a food preparation area during a food preparation process; determining at least one food preparation timer based on one or more parameters of the food preparation process; monitoring a duration of the food preparation process; comparing the duration of the food preparation process to the food preparation timer; and initiating a sanitization event when the duration of the food preparation process satisfies the food preparation timer, wherein initiating the sanitization event includes: controlling the at least one mechanical component of the food preparation apparatus to move the at least one food contact surface from one of a plurality of food preparation positions with respect to the food preparation area to a sanitization position within a sanitization chamber of an antimicrobial lighting fixture.

EXAMPLE 14. The method of Example 13 further comprising monitoring a duration of an antimicrobial light treatment received within the sanitization chamber.

EXAMPLE 15. The method of Example 13 further comprising monitoring an intensity of an antimicrobial light treatment received within the sanitization chamber.

EXAMPLE 16 The method of Example 15 further comprising controlling the at least one mechanical component of the food preparation apparatus to move the at least one food contact surface from the sanitization position within the sanitization chamber of the antimicrobial lighting fixture to one of the plurality of food preparation positions with respect to the food preparation area based on the monitored intensity of the antimicrobial light treatment.

EXAMPLE 17. The method of Example 16 further comprising determining a dosage of antimicrobial light received based on the monitored intensity of the antimicrobial light treatment.

EXAMPLE 18. The method of Example 13 the one or more parameters of the food preparation process include a type of the at least one food item.

EXAMPLE 19 A nonvolatile computer-readable storage medium storing instructions that, when executed, cause one or more processors to: control at least one mechanical component of a food preparation apparatus having at least one food contact surface to prepare at least one food item at a food preparation area during a food preparation process; determine at least one food preparation timer based on one or more parameters of the food preparation process; monitor a duration of the food preparation process; compare the duration of the food preparation process to the food preparation timer; and initiate a sanitization event when the duration of the food preparation process satisfies the food preparation timer, wherein initiating the sanitization event includes: controlling the at least one mechanical component of the food preparation apparatus to move the at least one food contact surface from one of a plurality of food preparation positions with respect to the food preparation area to a sanitization position within a sanitization chamber of an antimicrobial lighting fixture.

EXAMPLE 20. The nonvolatile computer-readable storage medium of Example 19 further storing instructions that, when executed, cause the one or more processors to: control the at least one mechanical component of the food preparation apparatus to move the at least one food contact surface from the sanitization position within the sanitization chamber of the antimicrobial lighting fixture to one of the plurality of food preparation positions with respect to the food preparation area based on the monitored intensity of the antimicrobial light treatment.

Various examples have been described. These and other examples are within the scope of the following claims.

The invention claimed is:
1. A system comprising:
an antimicrobial lighting fixture including:
an enclosure forming a sanitization chamber; and
one or more antimicrobial lighting segments, each antimicrobial lighting segment including one or more elements, wherein each element emits light within the sanitization chamber at a wavelength, irradiance, and direction sufficient to inactivate one or more microorganisms on a target surface within the sanitization chamber; and
an automated food preparation apparatus including:
at least one mechanical component controllable to prepare at least one food item and comprising at least one food contact surface; and
a controller comprising computer readable instructions configured to be executed on one or more processors to control the at least one mechanical component to move at least one food contact surface from a food preparation position to a sanitization position within the sanitization chamber,
wherein the antimicrobial lighting fixture controls each antimicrobial light segment based on food preparation information received from the automated food preparation apparatus.

2. The system of claim 1 wherein each of the one or more antimicrobial lighting segments are individually controllable by the antimicrobial lighting fixture.

3. The system of claim 1 wherein the antimicrobial lighting fixture further comprises a presence sensor that detects presence of at least a portion of the automated food preparation apparatus within the sanitization chamber.

4. The system of claim 1 wherein the antimicrobial lighting fixture further comprises one or more sensors that detect an intensity of antimicrobial light emitted within the sanitization chamber.

5. The system of claim 4 wherein the antimicrobial lighting fixture further includes a controller connected to receive the detected intensity of the antimicrobial light emitted within the sanitization chamber and that generates a lamp replacement notification when the detected intensity is below a threshold.

6. The system of claim 4 wherein the antimicrobial lighting fixture further includes a controller connected to receive the detected intensity of the antimicrobial light emitted within the sanitization chamber and that controls a duration of an antimicrobial light treatment received within the sanitization chamber by the at least one food contact surface of the automated food preparation apparatus based on the detected intensity.

7. The system of claim 1 wherein the automated food preparation apparatus includes a plurality of food contact surfaces, and wherein the one or more antimicrobial lighting segments are controllable to direct light at a wavelength and irradiance sufficient to inactivate one or more microorganisms on one or more of the plurality of food contact surfaces when the one or more food contact surfaces are present within the sanitization chamber.

8. The system of claim 1 wherein at least one of the antimicrobial lighting segments includes a plurality of light-emitting diode (LED) elements, and wherein each LED element emits light including wavelengths in a range of about 405±15 nanometers.

9. The system of claim 1 wherein at least one of the antimicrobial lighting segments includes one or more lighting elements that emit light in a short-wavelength ultraviolet (UV-C) wavelength range of 200-300 nm.

10. The system of claim 1 wherein at least one of the antimicrobial lighting segments includes one or more elements that emits light including one or more wavelengths in a first wavelength range and at least one other of the antimicrobial lighting segments includes one or more elements that emit light including one or more wavelengths in a second wavelength range.

11. The system of claim 1 wherein the one or more microorganisms include at least one of *Bacillus* spp., *Pseudomonas* spp., *Listeria, Staphylococcus aureus, Salmonella* spp., *E. coli*, coliforms, *Legionella* spp., *Acinetobacter* species, *Candida* spp., *Saccharomyces* spp., *Aspergillus* spp., *Alcaligenes, Flavobacterium, Campylobacter* spp., *Clostridium perfringens, Clostridium botulinum, Shigella* spp., *Vibrio* spp., noroviruses, or hepatitis A.

12. The system of claim 1 wherein the food preparation information includes a type of food being prepared.

13. The system of claim 1 wherein the food preparation information further includes one or more information regarding a time of day, an amount of time the at least one mechanical component has been prepared the food, or the amount of time since a last sanitization procedure was performed.

14. A system comprising:
an antimicrobial lighting fixture including:
an enclosure forming a sanitization chamber; and
one or more antimicrobial lighting segments, each antimicrobial lighting segment including one or more elements, wherein each element emits light within the sanitization chamber at a wavelength, irradiance, and direction sufficient to inactivate one or more microorganisms on a target surface within the sanitization chamber; and
an automated food preparation apparatus including:
at least one mechanical component controllable to prepare at least one food item and comprising a plurality of food contact surfaces; and
a controller comprising computer readable instructions configured to be executed on one or more processors to control the at least one mechanical component to move at least one food contact surface from a food preparation position to a sanitization position within the sanitization chamber,
wherein the one or more antimicrobial lighting segments are controllable to direct light at a wavelength and irradiance sufficient to inactivate one or more microorganisms on one or more of the plurality of food contact surfaces when the one or more of the plurality of food contact surfaces are present within the sanitization chamber.

15. The system of claim 14 wherein each of the one or more antimicrobial lighting segments are individually controllable by the antimicrobial lighting fixture.

16. The system of claim 14 wherein the antimicrobial lighting fixture further comprises a presence sensor that detects presence of at least a portion of the automated food preparation apparatus within the sanitization chamber.

17. The system of claim 14 wherein the antimicrobial lighting fixture further comprises one or more sensors that detect an intensity of antimicrobial light emitted within the sanitization chamber.

18. The system of claim 17 wherein the antimicrobial lighting fixture further includes a controller connected to receive the detected intensity of the antimicrobial light emitted within the sanitization chamber and that generates a lamp replacement notification when the detected intensity is below a threshold.

19. The system of claim 17 wherein the antimicrobial lighting fixture further includes a controller connected to receive the detected intensity of the antimicrobial light emitted within the sanitization chamber and that controls a duration of an antimicrobial light treatment received within the sanitization chamber by the one or more of the plurality of food contact surfaces of the automated food preparation apparatus based on the detected intensity.

20. The system of claim 14 wherein at least one of the antimicrobial lighting segments includes a plurality of light-emitting diode (LED) elements, and wherein each LED element emits light including wavelengths in a range of about 405±15 nanometers.

21. The system of claim 14 wherein at least one of the antimicrobial lighting segments includes one or more lighting elements that emit light in a short-wavelength ultraviolet (UV-C) wavelength range of 200-300 nm.

22. The system of claim 14 wherein at least one of the antimicrobial lighting segments includes one or more elements that emits light including one or more wavelengths in a first wavelength range and at least one other of the antimicrobial lighting segments includes one or more elements that emit light including one or more wavelengths in a second wavelength range.

23. The system of claim 14 wherein the one or more microorganisms include at least one of *Bacillus* spp., *Pseudomonas* spp., *Listeria, Staphylococcus aureus, Salmonella* spp., *E. coli*, coliforms, *Legionella* spp., *Acinetobacter* species, *Candida* spp., *Saccharomyces* spp., *Aspergillus* spp., *Alcaligenes, Flavobacterium, Campylobacter* spp., *Clostridium perfringens, Clostridium botulinum, Shigella* spp., *Vibrio* spp., noroviruses, or hepatitis A.

* * * * *